(12) United States Patent
Lusted et al.

(10) Patent No.: US 9,711,060 B1
(45) Date of Patent: Jul. 18, 2017

(54) BIOMETRIC SENSOR RING FOR CONTINUOUS WEAR MOBILE DATA APPLICATIONS

(71) Applicant: Senstream, Inc., San Francisco, CA (US)

(72) Inventors: Hugh Lusted, Oregon House, CA (US); Jashojit Roy, San Francisco, CA (US); David W. Proctor, Emerald Hills, CA (US)

(73) Assignee: SENSTREAM, INC., San Francisco, CA (US)

( * ) Notice: Subject to any disclaimer, the term of this patent is extended or adjusted under 35 U.S.C. 154(b) by 0 days.

(21) Appl. No.: 14/799,487

(22) Filed: Jul. 14, 2015

Related U.S. Application Data

(60) Provisional application No. 61/998,959, filed on Jul. 14, 2014.

(51) Int. Cl.
| | |
|---|---|
| *G09B 19/00* | (2006.01) |
| *A61B 5/0205* | (2006.01) |
| *A61B 5/00* | (2006.01) |
| *A61B 5/0402* | (2006.01) |
| *G08B 21/04* | (2006.01) |
| *G06F 3/01* | (2006.01) |

(52) U.S. Cl.
CPC ............ *G09B 19/00* (2013.01); *A61B 5/0205* (2013.01); *A61B 5/681* (2013.01); *A61B 5/0006* (2013.01); *A61B 5/02055* (2013.01); *A61B 5/0402* (2013.01); *A61B 5/6826* (2013.01); *G06F 3/014* (2013.01); *G06F 2203/0331* (2013.01); *G08B 21/0446* (2013.01); *G08B 21/0453* (2013.01)

(58) Field of Classification Search
CPC ..... A61B 5/681; A61B 5/0205; A61B 5/6826; A61B 5/02055; A61B 5/0402; A61B 5/0006; G06F 2203/0331; G06F 3/014; G08B 21/0453; G08B 21/0446
USPC ................ 600/344, 300, 301, 509; 345/156; 361/679.03; 607/6
See application file for complete search history.

(56) References Cited

U.S. PATENT DOCUMENTS 5,964,701 A * 10/1999 Asada ................ A61B 5/02438
128/903
6,402,690 B1 6/2002 Rhee et al.
(Continued)

OTHER PUBLICATIONS

RingGuard, www.viewithere.com/ring_guard/, retrieved from Internet Wayback Machine, Jul. 25, 2011.*

*Primary Examiner* — Jack Yip
(74) *Attorney, Agent, or Firm* — O'Banion & Ritchey LLP; John P. O'Banion

(57) ABSTRACT

A biometric sensing apparatus for estimating the emotional state of a user. A self-contained biometric sensing ring is worn on the finger (or fingers) of the user during their normal activities. Biometric information is collected and sent wirelessly to the user's mobile device configured with application programming for analyzing and displaying the biometric information. The biometric ring is configured with sensors that the structure of the ring retains at a proper pressure against the finger of the user. The sensors comprise at least electrodermal response (EDR), photoplethysmograph (PPG), temperature, and acceleration. The ring has a self-contained power source, and is configured for adjustably fitting a wide range of users.

25 Claims, 18 Drawing Sheets

(56) References Cited

U.S. PATENT DOCUMENTS

| | | | |
|---|---|---|---|
| 6,608,562 B1* | 8/2003 | Kimura | A61B 5/02427 128/903 |
| 2005/0231686 A1* | 10/2005 | Rathjen | A61B 3/16 351/205 |
| 2008/0058622 A1* | 3/2008 | Baker | A61B 5/14552 600/344 |
| 2010/0081900 A1* | 4/2010 | Price | A61B 5/14552 600/324 |
| 2012/0218184 A1* | 8/2012 | Wissmar | G06F 3/0346 345/158 |
| 2013/0095459 A1* | 4/2013 | Tran | A61B 5/6816 434/247 |
| 2013/0183646 A1 | 7/2013 | Lusted et al. | |
| 2013/0226015 A1* | 8/2013 | Lam | A61B 5/6897 600/499 |
| 2014/0215684 A1* | 8/2014 | Hardy | A41D 19/0031 2/160 |
| 2015/0133193 A1* | 5/2015 | Stotler | G06F 1/163 455/557 |
| 2015/0220109 A1* | 8/2015 | von Badinski | G01P 15/00 340/539.12 |
| 2015/0327809 A1* | 11/2015 | Tateda | A61B 5/1172 600/324 |

* cited by examiner

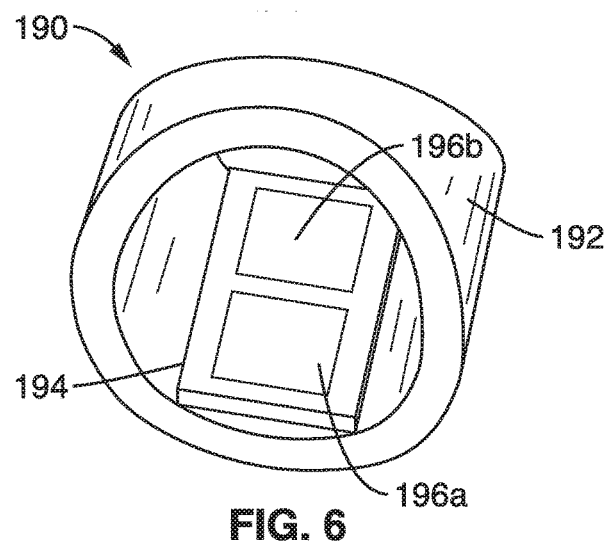
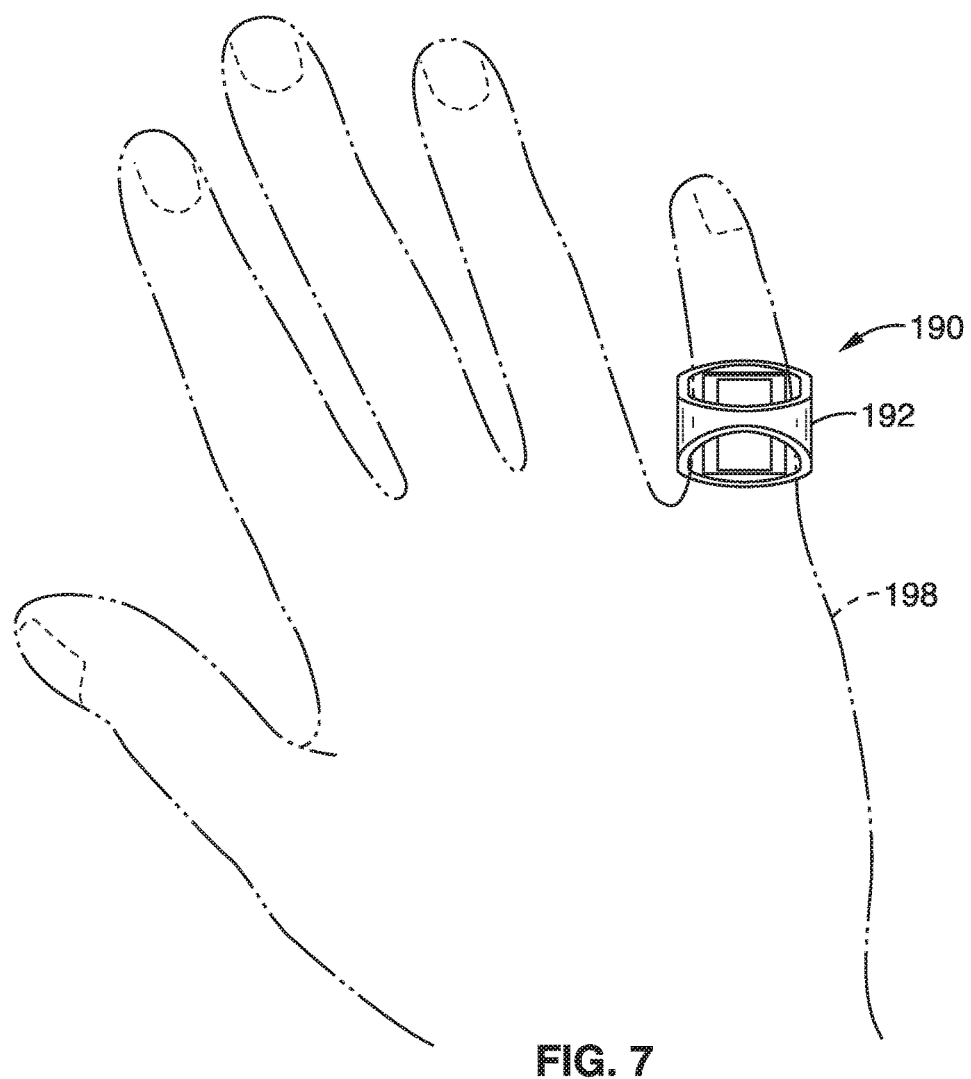
FIG. 6
FIG. 7

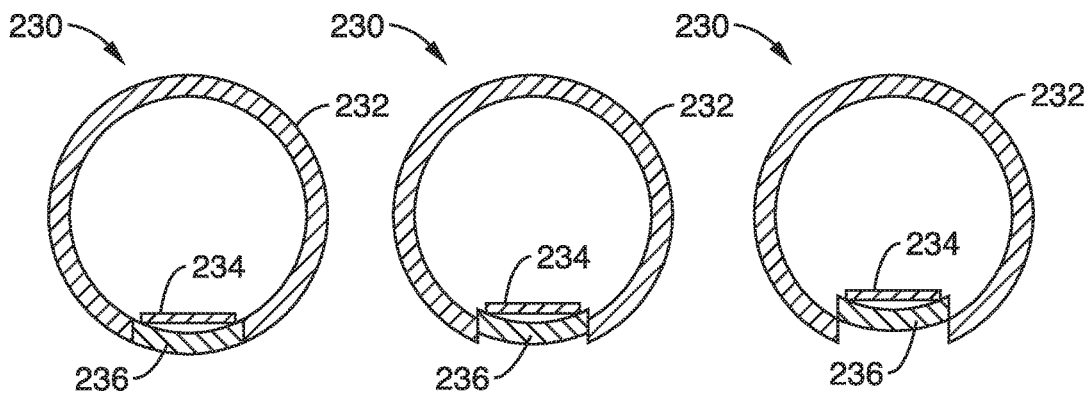
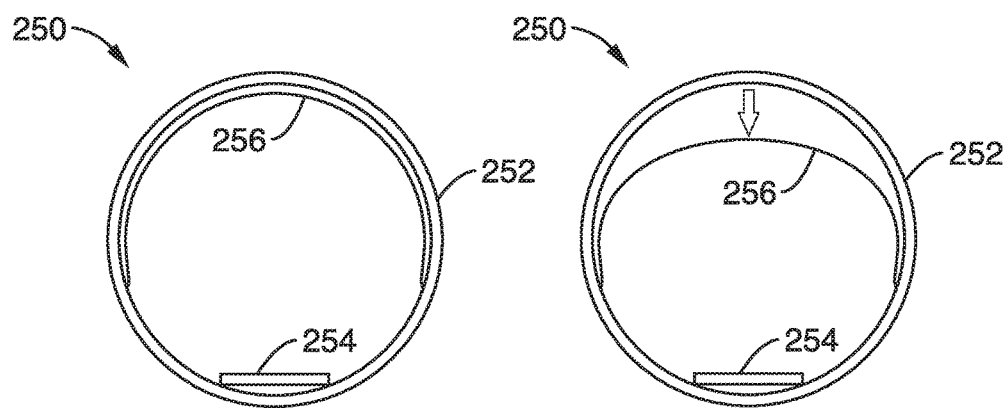
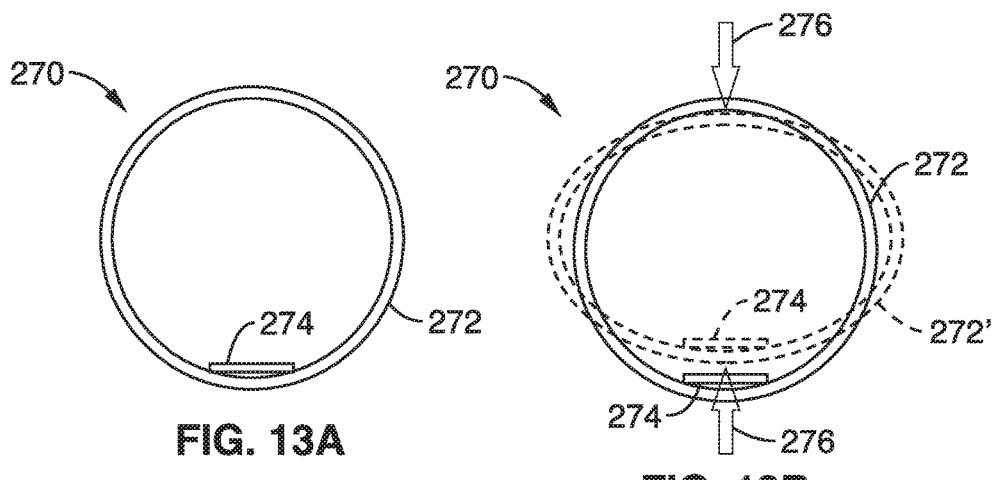

BIOMETRIC SENSOR RING FOR CONTINUOUS WEAR MOBILE DATA APPLICATIONS

CROSS-REFERENCE TO RELATED APPLICATIONS

This application claims priority to, and the benefit of, U.S. provisional patent application Ser. No. 61/998,959 filed on Jul. 14, 2014, incorporated herein by reference in its entirety.

STATEMENT REGARDING FEDERALLY SPONSORED RESEARCH OR DEVELOPMENT

Not Applicable

INCORPORATION-BY-REFERENCE OF COMPUTER PROGRAM APPENDIX

Appendix A referenced herein is a computer program listing in a text file entitled "SEN6468_05A_computer_program_listing_appendix_A.txt" created on Jul. 14, 2015 and having a 39 kb file size. The computer program code, which exceeds 300 lines, is submitted as a computer program listing appendix through EFS-Web and is incorporated herein by reference in its entirety.

NOTICE OF MATERIAL SUBJECT TO COPYRIGHT PROTECTION

A portion of the material in this patent document is subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. §1.14.

BACKGROUND

1. Technical Field

The disclosure pertains generally to biofeedback devices, and more particularly to biometric wearables for short, medium, and long term data acquisition and analysis applications.

2. Background Discussion

Electronic biofeedback equipment has long been available in various forms. Typically, these devices are configured for fulfilling a very specific and narrow role. For example, the electrodermal response (EDR) was first measured by the psycho-galvanometer, as it was called upon to measure skin resistance. The EDR device is best known as one element of a police style lie-detector. Some biofeedback devices today utilize the same circuitry and electrodes as utilized when this device was developed decades ago. The electrodermal response is the medically preferred term for galvanic skin response (GSR). Another specific device is the photoplethysmograph (PPG), which is well known in hospitals for quick assessment of heart rate based on sensing at the fingertip. However, these devices are generally directed to specific purposes in short term testing and not generally applicable for long term use and interaction with a user.

Accordingly, the present disclosure overcomes the limitations of these short term testing devices, while providing additional advantages.

BRIEF SUMMARY

The technology presented provides for placement of one or more biometric sensors on the finger, with the combination of sensor data allowing a determination of accurate assessments of the physiological and emotional state of the user within applications executing on a mobile device. A multichannel finger sensor system has been previously described by the Applicant as seen in U.S. Patent Application Publication No. US-2013-0183646-A1, which application and publication are incorporated herein by reference in their entireties.

In contrast to the above, the present disclosure describes a ring form factor with mechanical and electronic provisions that allow for continuous wear (e.g., outside of the confines of a test environment, such as while performing everyday activities) and proper fit on fingers of different sizes. To produce quality biometric data, the biometric sensors must maintain proper skin contact on the finger. Toward that objective the present disclosure describes several embodiments for a sensor ring configured to assure a proper fit with a user's finger, or fingers, so that sensors are retained with proper skin contact and pressure.

Advantageously, various embodiments of the technology described herein may incorporate one or more of the following elements: (a) multiple biometric sensors whose data can be combined and correlated to assess the physical and emotional state of the user; (b) mechanical innovation which allows the ring to be worn on many different finger sizes; and (c) inclusion of sufficient capacity energy storage (e.g., battery) to allow a user to wear the ring for extended periods of time (e.g., all day) which enables long term biometric data collection. This continuous data collection capability provides a new window on monitoring the autonomic nervous system (ANS) in real life situations. Presently ANS monitoring is only possible in a laboratory setting.

The technology can be implemented with dedicated hardware, or for the sake of simplicity of implementation, may be executed using existing electronic devices. By way of example and not limitation, instructions of an application program (or programs) may be loaded for execution on a general purpose electronic processing device, such as a mobile device (e.g., smart phone, tablet, notepad, netbook, laptop, etc.). In at least one implementation, no additional hardware or hardware changes are required on the mobile device side. Thus, a user need only obtain the emotion sensor device for attachment to their mobile device, and the desired application to execute from that mobile device.

Further aspects of the technology described herein will be brought out in the following portions of the specification, wherein the detailed description is for the purpose of fully disclosing preferred embodiments of the technology without placing limitations thereon.

BRIEF DESCRIPTION OF THE SEVERAL VIEWS OF THE DRAWING(S)

The technology described herein will be more fully understood by reference to the following drawings which are for illustrative purposes only:

FIG. 6 is an image rendering of a biometric sensing ring according to an embodiment of the present disclosure.

FIG. 7 is an image rendering of a biometric sensing ring being worn by a user according to an embodiment of the present disclosure.

FIG. 11A through FIG. 11C are cross section views of a biometric sensing ring having at least one perimeter element configured for displacement according to an embodiment of the present disclosure toward maintaining proper sensor-to-finger contact.

FIG. 12A and FIG. 12B are side views of a biometric sensing ring according to an embodiment of the present disclosure, shown using a memory material for assuring proper sensor-to-finger contact.

FIG. 13A and FIG. 13B are side views of a biometric sensing ring according to an embodiment of the present disclosure, shown incorporating a malleable material that can be formed to assure proper sensor-to-finger contact.

DETAILED DESCRIPTION

1. Overview

The continuous wearing biometric sensor of the present disclosure is configured to incorporate multiple sensor types, exemplified herein with five sensor types, into a package wearable on any finger of a user's hand. In one embodiment, the sensors and associated hardware are contained on a flexible board contained within the ring. The sensing ring can be worn on a finger in various ways, such as a ring worn on the third phalange (traditional ring position); and also as multiple rings (e.g., two or three rings) connected by a flexible circuit board for wear on two or three phalanges of the same finger, or rings integrated within a glove for monitoring signals from up to five fingers at once.

According to at least one embodiment of the technology described herein, an emotion sensor comprises sensors which include the following. (a) An EDA (electrodermal activity) sensor is incorporated for measuring user arousal and relaxation, with phasic sensing (a.k.a. EDR—electrodermal response) and tonic sensing (a.k.a. EDL—electrodermal level) being derived from this sensor. The EDA sensor contacts the palm side of the finger where there is the greatest density of eccrine sweat glands that respond to sympathetic nervous system activation. (b) A PPG (photoplethysmograph) sensor is incorporated for measuring user cardiac pulse, with heart rate (HR) and heart rate variability (HRV) being derived from PPG sensor data. (c) A temperature sensor (e.g., thermistor) is incorporated for measuring skin temperature. (d) A 3-D accelerometer sensor is incorporated into the device to sense accelerations in three spatial dimensions (movement) in response to user finger movement. (e) A chemical sensor is incorporated that can detect certain chemical levels in user sweat from the eccrine glands, such as blood sugar, cortisol, and/or metabolic products from drugs or hormones. It should be appreciated, however, that the biometric sensor ring of the present disclosure may include less or more sensors without departing from the teachings of the present invention.

2. Circuit Board And Sensor Surface

Figure 1A:
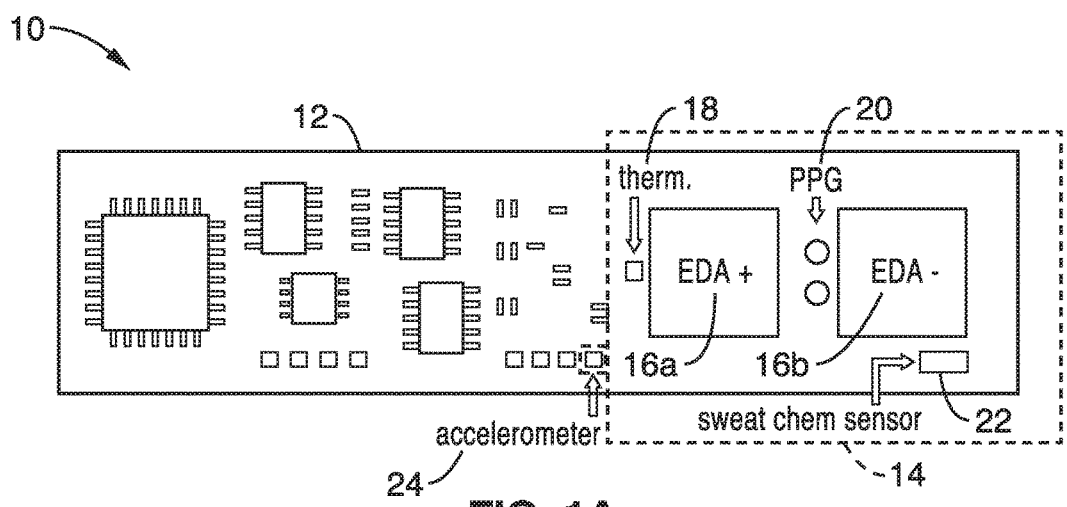
FIG. 1A and FIG. 1B are rendered images of electronic circuitry contained within a biometric sensing ring according to an embodiment of the present disclosure.

FIG. 1A illustrates an example embodiment 10 of a sensor circuit comprising a multi-sensor circuit board 12, with sensor surface section 14. EDA plus (+) 16a and EDA minus (−) 16b electrodes are retained in this area, along with a thermistor (therm.) 18, a PPG infrared 20 (e.g., IR light source and IR receiver), a chemical sensor 22 (e.g., nanotubule type) for detecting molecular compounds in sweat, and a 3D accelerometer 24. It should be noted that the various sensors, including the chemical sensor can be alternatively located at other points on the circuit board as long as the sensor element is in contact with the skin. Also the accelerometer can be located anywhere within the ring enclosure and does not require skin contact.

Figure 1B:
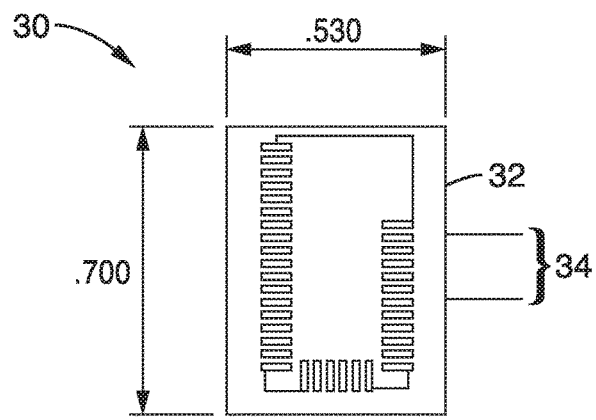

FIG. 1B depicts a module 30 containing a circuit board 32 with pads upon which Bluetooth Low Energy (BLE) chip is mounted with connection 34. Circuit board 32 is constructed on a flexible substrate to fit the inside of the ring enclosure, and attached to the circuit board 12 of FIG. 1A.

3. Ring Configuration with Flex Circuit Board

Figure 2A:
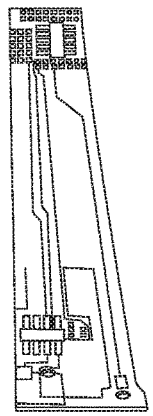
FIG. 2A through FIG. 2C are rendered images of a biometric sensing ring according to an embodiment of the present disclosure shown formed using flexible circuitry.
Figure 2B:
Figure 2C:
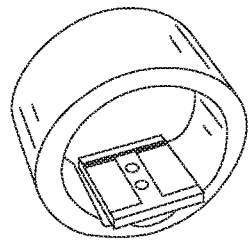

FIG. 2A through FIG. 2C show a sample flex board in FIG. 2A, with the board flexed into a circle in FIG. 2B, and an example ring model with material surrounding the flexed circuit board but having the sensor surface exposed so that it contacts the skin on the palm side of the finger in FIG. 2C. The sensor surface shown here in the ring is similar to that shown diagrammatically in FIG. 1A.

Figure 3:
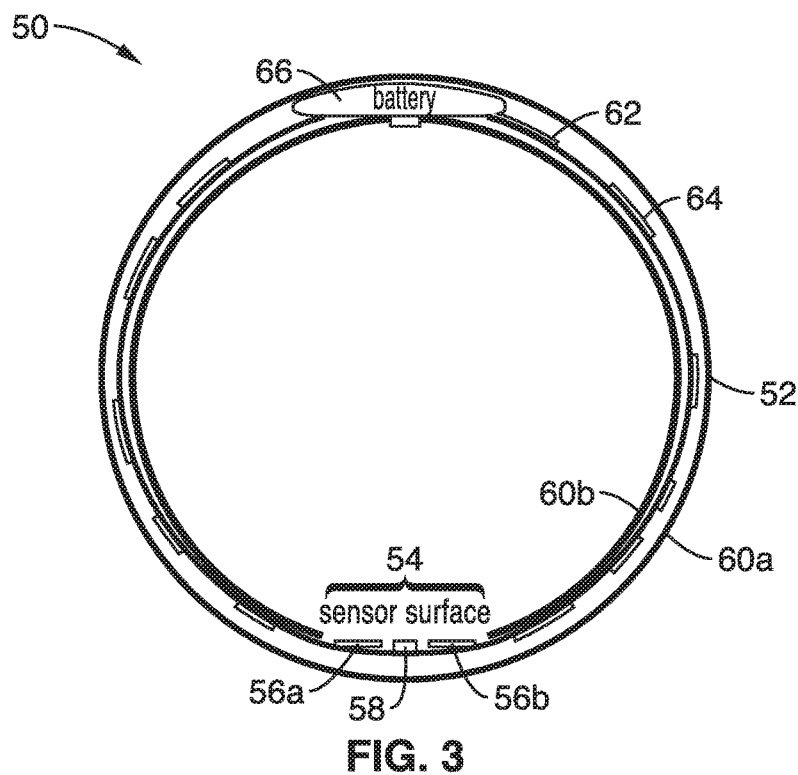
FIG. 3 is a side view cross-section of a biometric sensing ring according to an embodiment of the present disclosure, showing sensors disposed toward the interior opening of the ring and operating circuitry disposed internally within the periphery of the ring.

FIG. 3 illustrates an example embodiment 50 of a ring enclosure with the flex board inside shown in cross section. The ring body 52 is shown with sensor surface 54 exposed on an inner ring surface depicted with EDA contacts 56a, 56b, and other sensors 58 (e.g., temperature and/or chemical sensor). An exterior material 60a, 60b is shown on the exterior surrounding a flexible circuit board 62 upon which are connected various circuit elements (chips) 64, and battery 66. It should be appreciated that the processor, op amps, memory, BLE module, battery, and passive components are all preferably distributed along the board to allow flex spaces between the components. It is also preferable that the sensor surface be mounted on the bottom interior of the ring to provide reliable contact with the skin of the user's finger. The design allows for a comfortable fit and also minimizes motion artifacts generated by skin/sensor movement. Mechanisms for optimizing fit for different fingers will be described in the next section. It will be noted that a portion of the sensor, in particular the chemical sensor, is seen in FIG. 3 mounted on the top interior of the ring, as thermally active perspiration sweat glands are located on the top of the hand and fingers. Although it should be appreciated that the embodiments may be configured with the various sensor distributed in any desired positions along the circuit without departing from the teachings of the present disclosure.

Figure 4:
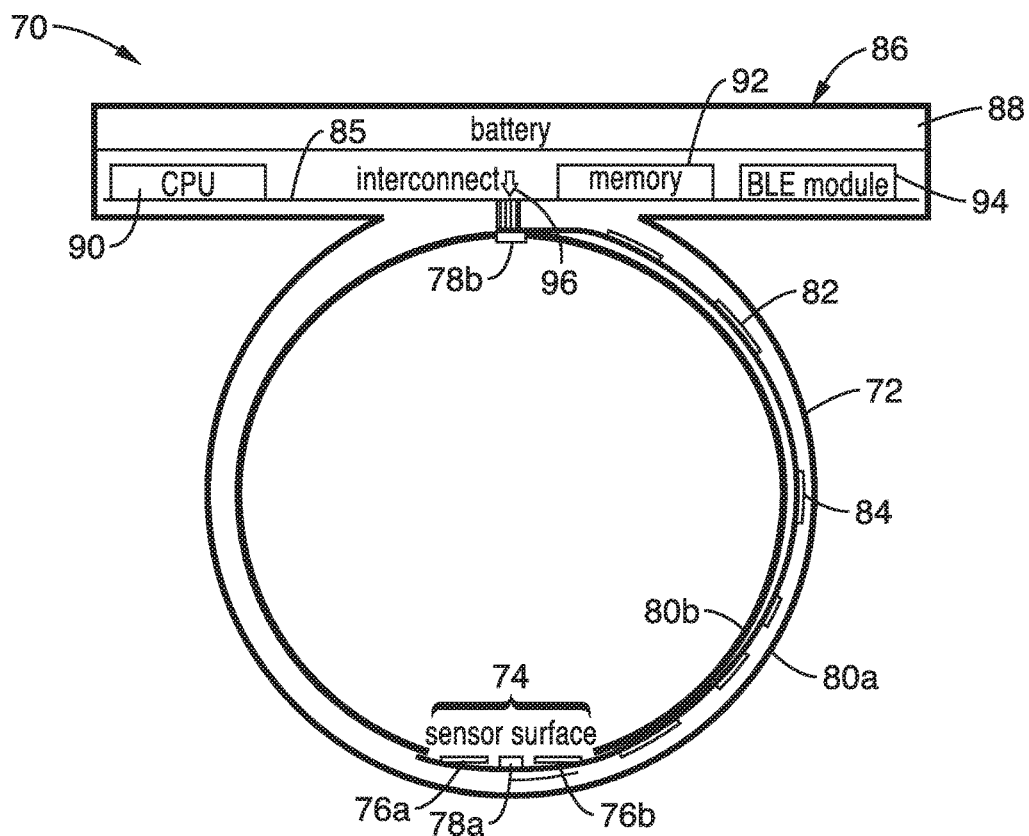
FIG. 4 is a side view cross-section of a biometric sensing ring according to an embodiment of the present disclosure, shown having an extended upper portion for housing the battery and certain other circuitry.

FIG. 4 illustrates an example embodiment 70 of an alternative ring configuration for the flex board wherein the main portion of the board is located in an enclosure on top of the ring. The ring body 72 is shown with sensor surface 74 exposed on an inner ring surface depicted with EDA contacts 76a, 76b, and other sensors 78a, 78b. An exterior material 80a, 80b is shown on the exterior surrounding a flexible circuit board 82 upon which are connected various circuit elements (chips) 84. However, unlike the circuit in FIG. 3, in this example the ring has an upper housing portion 86. In this upper housing 86, the flex board 82 traverses half the diameter of the ring and electrically connects through interconnect 96 to a top board 85. Upper housing 86 is seen with a CPU 90, memory 92, BLE module 94 connected to top board 85, while also retaining a battery 88 which can provide a significantly higher capacity than a battery comfortably retained within the back band of the ring. In this example of a flex board spanning half the circumference of the ring, the sensor surface is located at the end of the board with signal lines and a few components on the flex portion. It should be appreciated that this configuration is capable of supporting more memory and a larger battery. In wearability tests of the present disclosure, we have found that the top module can be up to twice the diameter of the finger (approx. 1.5 inches) in a round or square configuration without interfering with finger motion, such as typing or using manual equipment. The modules shown for CPU, memory, and BLE do not represent actual component sizes. Different package sizes are available for each of these components.

4. Multi-Sensor Circuit Architecture

Figure 5A:
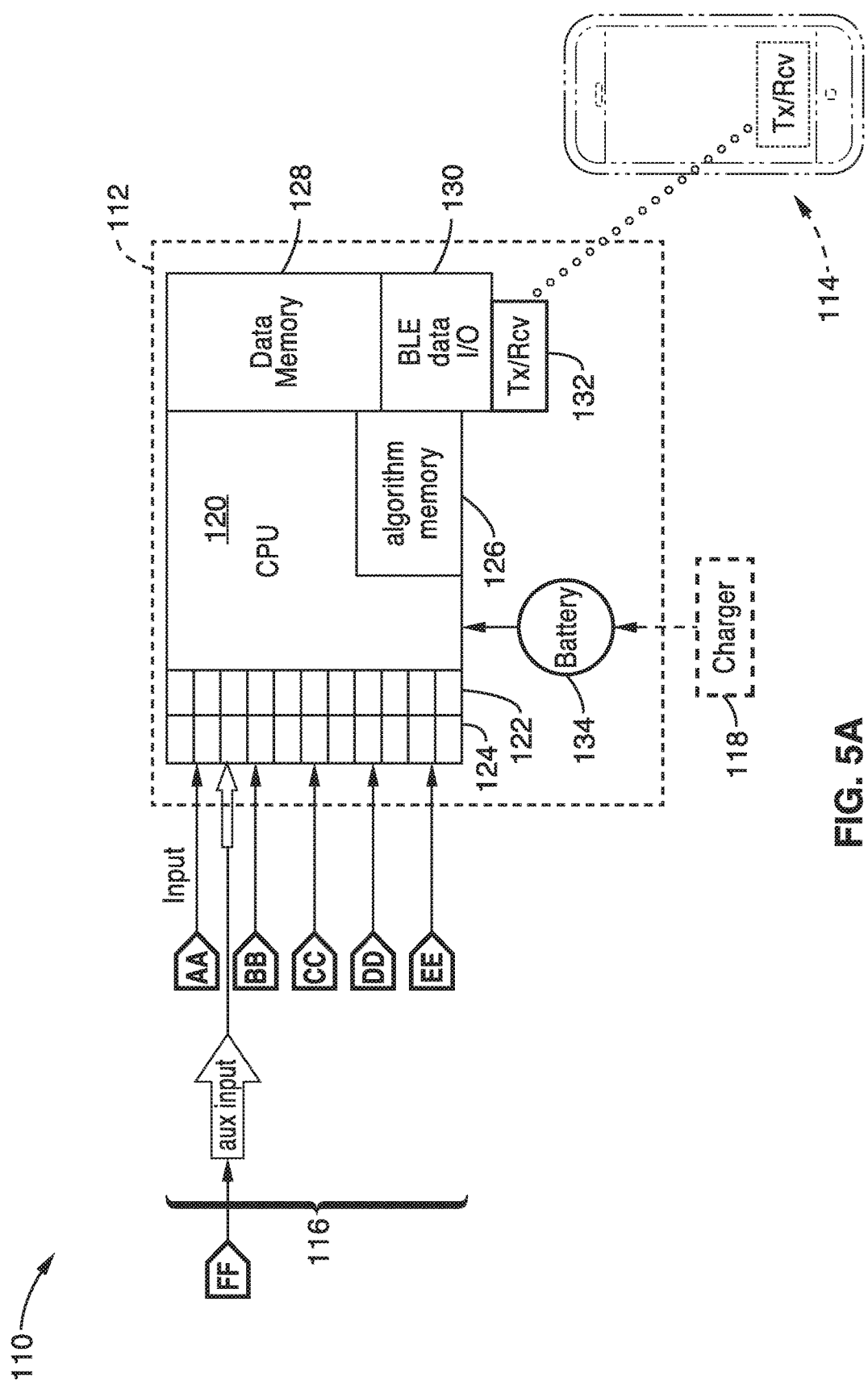
FIG. 5A and FIG. 5B are a biometric sensor circuit data capture and processing architecture with interconnection according to an embodiment of the present disclosure.
Figure 5B:
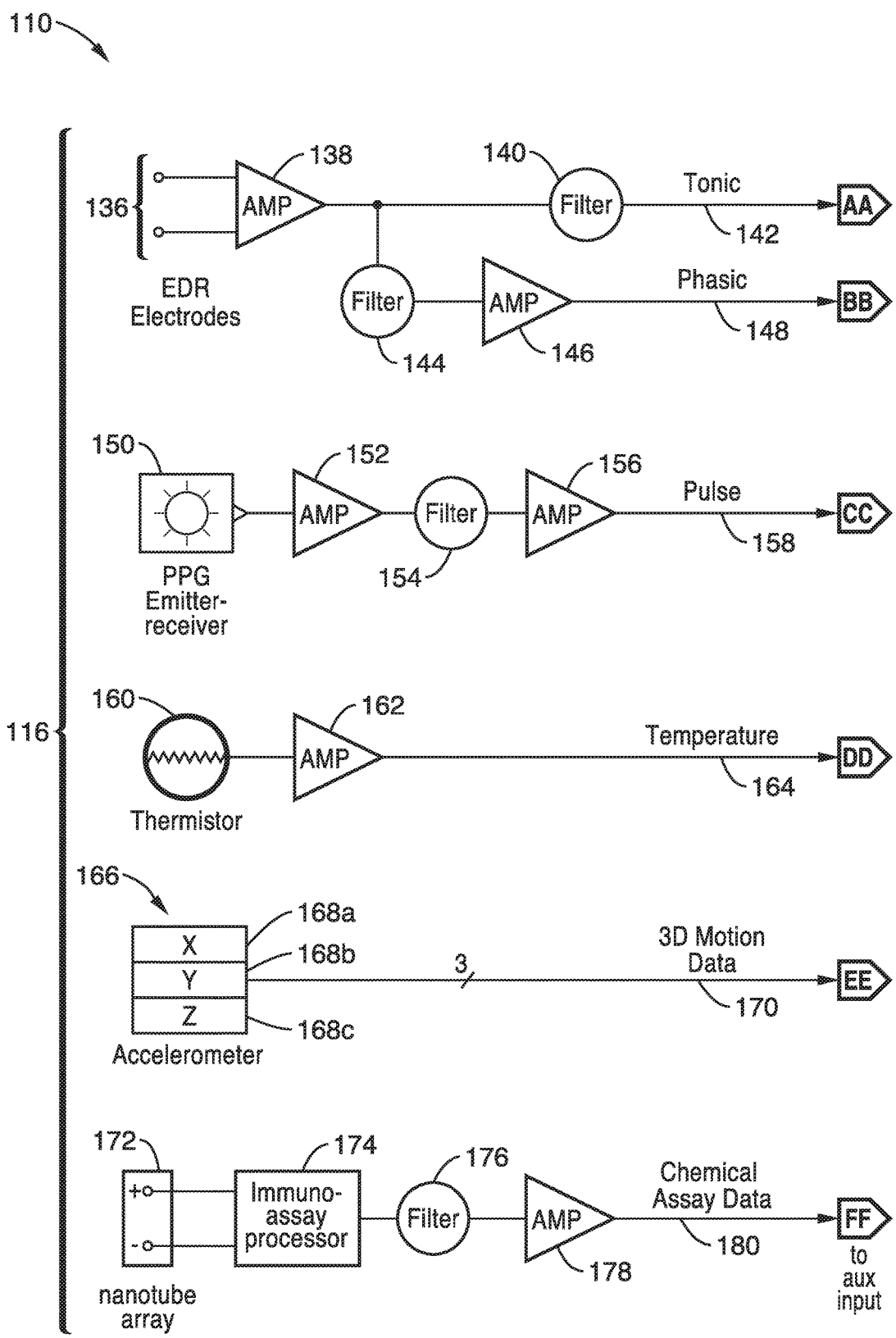

FIG. 5A and FIG. 5B illustrate an example embodiment 110 showing sensor circuit data capture and processing architecture with interconnection of circuit elements 112 of the various sensors 116 on the board and auxiliary inputs to a mobile device 114 through a wireless communication connection.

In FIG. 5B a series of inputs 116 is seen, including an EDA sensor utilizing two electrodes 136 that register changes in skin resistance. The signals are received by an amplifier 138 which outputs through two different filters 140, 144. The EDA signal is divided into two different channels: tonic 142 and phasic 148. The tonic is a more slowly varying DC signal and the phasic gives a faster response with user arousal and relaxation. The basic EDA signal is seen being filtered 140 through a low pass filter to directly generate tonic signal 142, while the higher frequency phasic signal is derived from a high pass filter 144 and preferably additional amplification 146 to output the phasic signal 148.

The PPG sensor 150 in at least one embodiment utilizes an infrared (IR) photo sensing emitter-receiver (e.g., sensitive photo-transistor) that produces a small voltage with IR illumination. Blood perfusion in the finger produced by cardiac pulse causes the IR light to be scattered and thus the IR detector's output varies with pulse. The IR signal is amplified 152, 156 and filtered 154, before outputting a pulse signal 158 to the processor. The thermistor 160 is a resistive element having a resistance value that changes with temperature. Output from the thermistor (or other temperature sensing device) is preferably amplified 162 and optionally conditioned as desired to generate a temperature signal 164.

The accelerometer 166 may be placed at any convenient location in the ring structure and it senses multiple axes of motion, such as seen for the X, Y, and Z axis 168a, 168b, 168c as 3D motion data 170 to the processor. In one implementation, the accelerometer generates a time varying voltage corresponding to the three axes of movement. Actually in this particular embodiment, each axis forms a separate data input to the processor, but the diagram shows one channel for the sake of simplicity of illustration.

The chemical sensor 172, senses selected chemical elements and generates a chemical sensing signal 180 to the processor. In at least one embodiment this chemical sensor comprises a programmable electro-immuno assay device 174 that generates a small voltage when a chemical match is found between a target molecule and the carbon nanotubule array containing the assay substrate. Output from electro-immuno assay device 174 is then filtered 176 and amplified 178 prior to outputting chemical assay data 180 to the processor, such as using an auxiliary input. Embodiments of the sensing ring preferably orient the chemical sensor so that it is adjacent the upper surface of the user's finger. Any of the embodiments of the present disclosure can include these small chemical sensors within the group of sensors either near the EDA electrodes (e.g., to contact the lower surface of the finger) or in a different area of the sensor ring, such as near its upper portion (e.g., to contact the upper surface of the finger).

Returning to FIG. 5A, it is seen that the received inputs 116 are preferably conditioned, typically including amplification and/or filtering 124, followed by conversion to a digital signal, such as by an analog-to-digital converter 122, prior to receipt by a processing unit 120 (e.g., CPU, microprocessor, microcontroller, DSP, or one or more electronic devices configured to process the sensor signals). Instructions for execution by the processor (or processors) and data, are stored in one or more memories 126, 128. The CPU runs signal processing methods for analyzing features of the multi-sensor data stream. Results of signal processing and raw data itself can be stored in the data memory (DM).

It will also be appreciated that the computer readable media (memory storing instructions) in both the biometric sensor ring and external applications to which it communicates, are computation systems with memory that are "non-transitory", that is to say they may comprise any and all forms of computer-readable media, with the sole exception being a transitory, propagating signal. Accordingly, the disclosed technology may comprise any form of computer-readable media, including those which are random access (e.g., RAM), require periodic refreshing (e.g., DRAM), those that degrade over time (e.g., EEPROMS, disk media), or that store data for only short periods of time and/or only in the presence of power, with the only limitation being that the term "computer readable media" is not applicable to an electronic signal which is transitory.

By way of example and not limitation, at least one embodiment of the instruction programming (e.g., firmware) is configured for scanning PPT and EDA sensors at 20 Hz with voltage level data streamed to application programming which executes on a remote device 114, preferably a smart phone. In one embodiment the BLE module contains the firmware memory, although various other memory configurations can be utilized without departing from the present disclosure. Embodiments of the application programming for smart phones have already been developed for iOS and Android operating systems. This application which executes from the smart phone can perform a wide variety of bio-sensing data collection, analysis, and display functions. For example, one embodiment of firmware records a time stamp, records EDA level every 50 msec, records PPT level every 50 msec, determines and records instantaneous heart rate (HR), average HR, and HR variability. Appendix A contains source code for an embodiment of software that runs on an Android platform.

The input gains are adjustable depending on the level of the input sensor signal, which can vary more than a factor of 500 (100 µV for EDA versus 50 mV for accelerometers), so the input stage is shown configured to scaling for these large differences. The analog signals are converted to digital signals in the processor A/D (analog to digital converter). The sampling rate of each channel can be independently set depending on the bandwidth of the input signal.

A wireless communication protocol is also supported as exemplified with a BlueTooth Low Energy (BLE) device 130 coupled to a transmitter/receiver 132 shown for wirelessly communicating with another electronic device which can allow for controlling device operation, registering collected sensor data, analyzing collected data, displaying collected data or analyzed data, or any combination thereof. It will be appreciated that many modern BLE modules contain the radio (Tx/Rcv), wherein there is no need for the separate Tx/Rcv 132 shown in the figure. Data can be uploaded to an external network at any time, such as via the exemplified BLE I/O module. The BLE module utilized in the example embodiment contains its own processor and memory and can be configured for different types of network protocols aside from the BlueTooth protocol. New signal processing algorithms can be downloaded to program memory in the CPU via the BLE module. In this current implementation version of the ring, the BLE module contains the A/Ds, processor, memory (e.g., instruction programming, firmware), transmit/receive radio, and antenna.

A self-contained power source 134, exemplified as a battery, is shown for powering the ring sensing device, and is shown with an optional charger 118, thus allowing the user to move about during the course of their normal activities.

5. Ring Form Factors and Wear-Ability

FIG. 6 illustrates an example embodiment 190 of biometric sensor ring in the described sensor board configuration. The ring housing 192 is seen with the sensor contact area 194 at the bottom surface of the ring with EDA contacts 196a, 196b.

FIG. 7 illustrates the ring embodiment 190 depicted in its proper placement on a finger having the sensor board on the bottom surface (palm side) of a hand 198.

Figure 8:
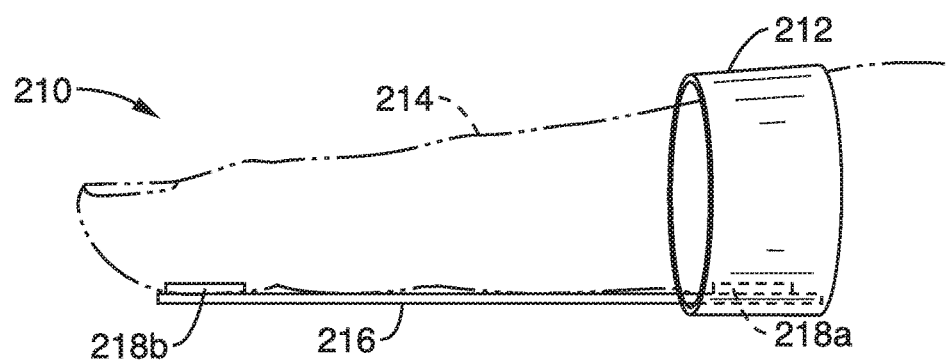
FIG. 8 is an image rendering of a biometric sensing ring with an extended sensing element as worn by a user according to an embodiment of the present disclosure.

FIG. 8 illustrates an example embodiment 210 of the biometric sensor ring which is configured to utilize the latest generation of biosensors, such as MC10 artificial skin, which is capable of supporting various types of chemical and molecular sensors. The ring housing 212 is seen on a finger 214 with circuits and sensors 218a, 218b along a flexible circuit 216. This embodiment takes advantage of the sensor input circuitry in the ring while greatly expanding the skin contact surface area for incorporating more sensor types as well as increasing the signal/noise for the EDA and PPG sensors. The artificial skin is unencumbering and disposable after one to two days.

Figure 9:
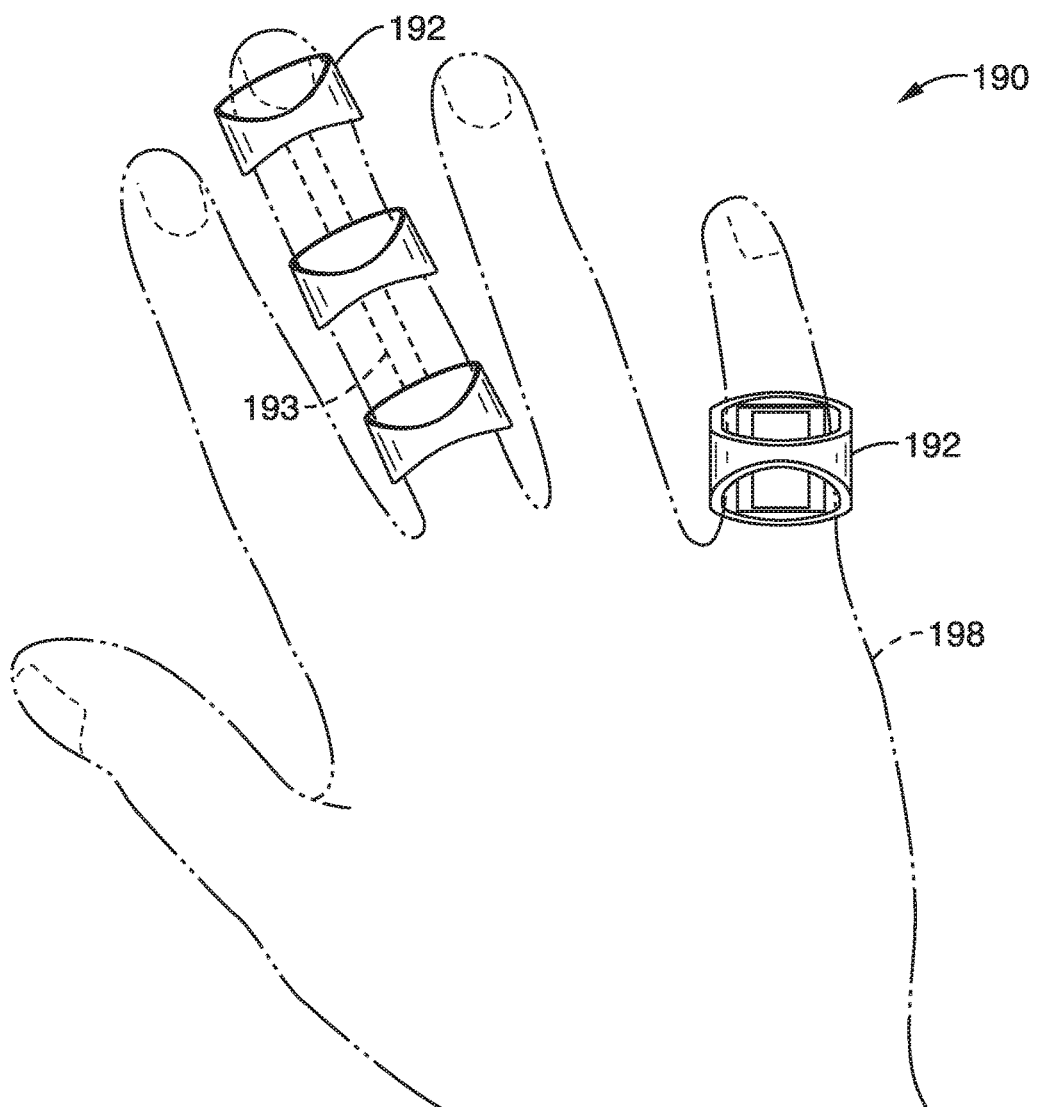
FIG. 9 is an image rendering of a user wearing multiple biometric sensing rings according to an embodiment of the present disclosure.

FIG. 9 illustrates an example embodiment 190 depicting multiple rings 192, three in this example, joined by a signal line flex board 193 and retained on a single finger 198. Certain use cases may require the increased surface area and sensor stability provided by this multiple ring configuration. It should be appreciated that this configuration operates with two or more ring elements, while the multiple rings may be alternatively or additionally worn on two or more fingers.

Figure 10:
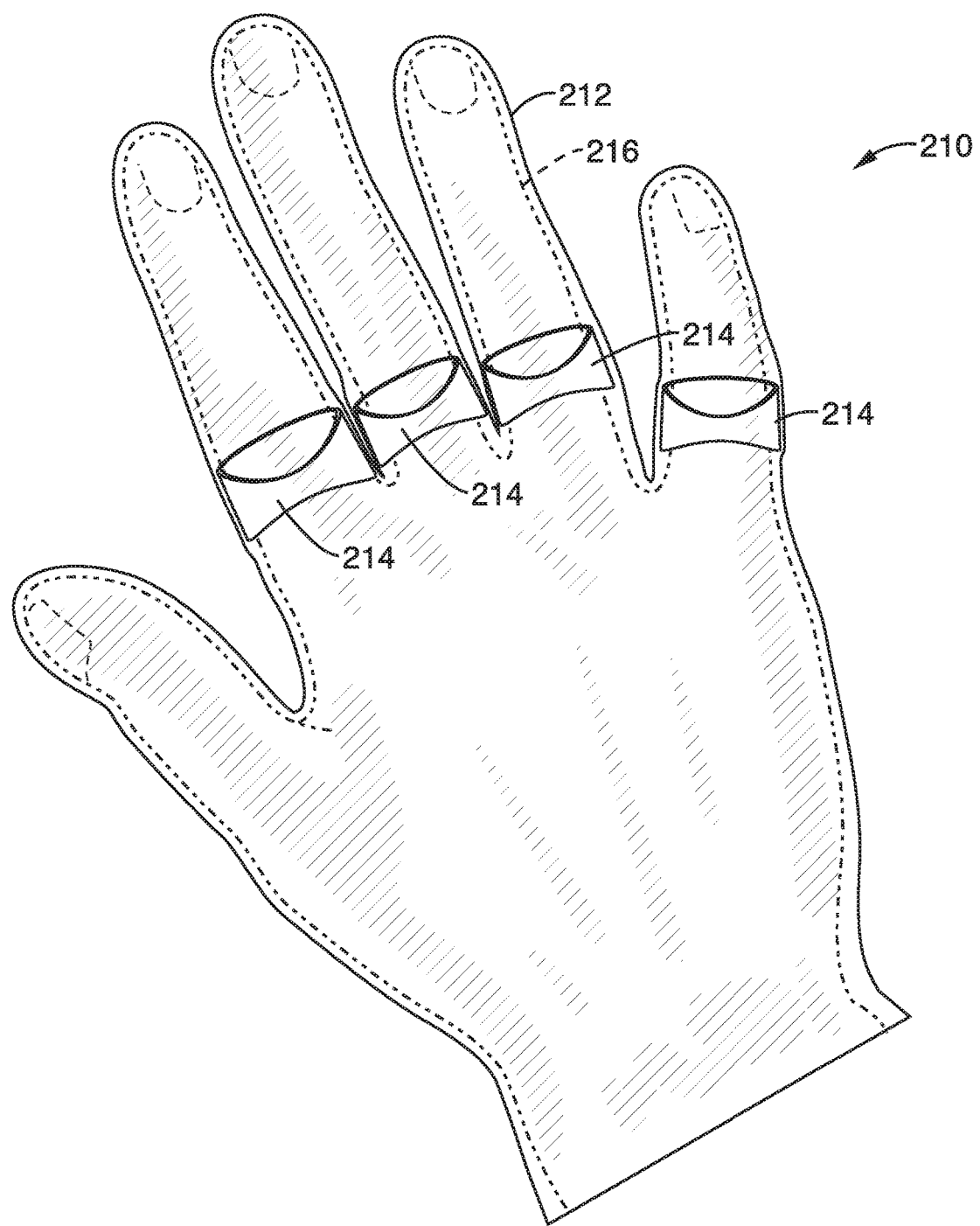
FIG. 10 is an image rendering of biometric sensing rings incorporated within a biometric sensing glove according to an embodiment of the present disclosure.

FIG. 10 illustrates an example embodiment 210 of a ring sensor glove. Multiple ring sensors 214 are retained within a glove material 212 configured for being retained over the hand 216 of a user. In this case, the same ring enclosure as shown in the previous figures can be sewn into the glove or the flex board itself can be incorporated in the fabric of the glove. Although only one ring is shown incorporated in each finger of the glove, it should be appreciated that multiple rings may be on a single finger or otherwise placed for engagement with user fingers as desired by the type of sensing being performed. With this glove design, the sensor elements can be positioned on any finger(s) and phalange(s).

6. Effective Skin Contact and User Comfort

In this section various solutions are offered for creating variable ring geometry to accommodate different sized fingers while offering comfortable fit for the user.

The sensor surface must be in stable contact with the skin in order to acquire optimal EDA and PPG data. Relative motion between the skin and sensor produces voltage spikes (artifacts) in the data record. These artifacts can be filtered out or eliminated by signal cancelling techniques, such as based on motion data from the accelerometers. However, it should be appreciated that it is still desirable to obtain the highest quality analog data at the input stage by optimizing the stability of the sensor surface.

FIG. 11A through FIG. 11C illustrate an example embodiment 230 of a sensor ring with a movable ring portion sensor surface (exaggerated displacement) that can press firmly against the lower surface of the finger, such as in response to a biasing member or manual locking into detent positions. A ring structure 232 is seen with the sensor board 234 retained in the interior of the ring on a movable ring section 236, which in this embodiment is configured to slide with a ratchet (detent position engagement structure) to engage the digit in response to applied manual pressure. The flex board accommodates this ring section 236 movement with a small ratchet on each side of the movable section holding the surface in place. The section can be released by pressing both sides of the ring simultaneously to disengage the ratchets.

FIG. 12A and FIG. 12B illustrate another variable geometry sensor ring embodiment 250 utilizing an expanding "memory" foam 256 on the inside upper surface of the ring housing 252. For example, one embodiment of the present disclosure utilizes a memory foam 256 that is similar to that used for ear plugs. To utilize this embodiment, the user squeezes the foam against the upper surface of the ring, resulting in a first ring aperture size as seen in FIG. 12A. The user inserts a finger and allows the foam to expand, as seen in FIG. 12B, against the upper part of the finger which places the lower surface firmly against the sensor section 254.

FIG. 13A and FIG. 13B illustrates an example embodiment 270 of a deformable sensor ring enclosure 272 that is made of malleable material. In FIG. 13A the ring 272, with sensor board 274, is seen in its initial configuration. In this embodiment, simply squeezing the ring 272 itself on the top and bottom as seen in FIG. 13B in response to force 276 places the sensor section in snug contact with the lower surface of the finger by changing the shape of the malleable ring from 272 to 272'. Releasing the ring from the finger requires only the application of sufficient pressure to the sides of the ring.

Figure 14A:
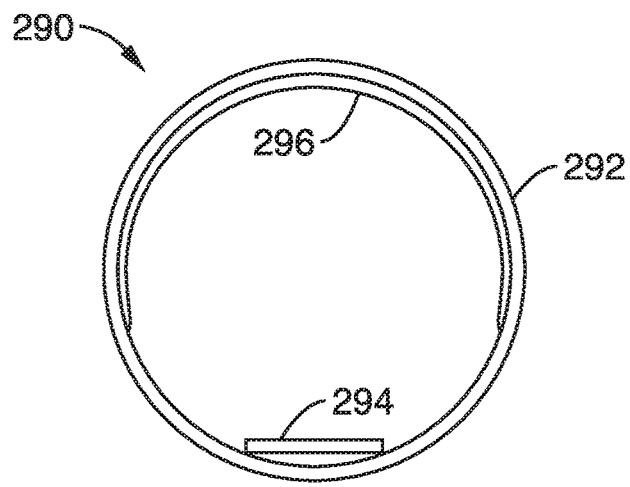
FIG. 14A and FIG. 14B are side views of a biometric sensing ring according to an embodiment of the present disclosure, shown utilizing a pneumatic arrangement for assuring proper sensor-to-finger contact.
Figure 14B:
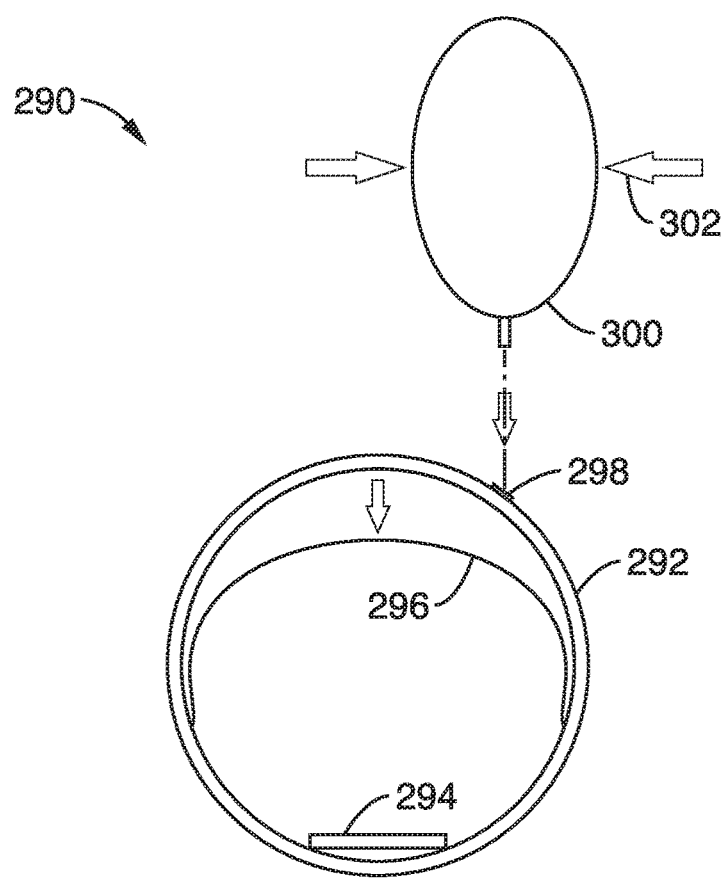

FIG. 14A and FIG. 14B illustrate an example embodiment 290 of a biometric sensor ring having a housing 292 incorporating a pneumatic collar 296 within the interior of the ring, preferably located in the top inside surface so that pressure is applied to press the finger into the sensors 294 located at the bottom inside surface of the ring. In FIG. 14A, the ring 290 is shown prior to inflation of the pneumatic collar. In FIG. 14B, a small squeeze bladder 300 is shown configured for engagement with a recessed valve 298. Pumping pressure 302 applied to the exterior of the bladder 300 results in expanding pneumatic collar 296 to the desired extent so that the user's finger is pressed against the sensors 294. The air can be released by engaging an air release mechanism either on the housing 292 or the bladder 300. This mechanism is also particularly well-suited for use for engaging bio-sensors on larger extremities (e.g., wrist, ankle, etc.).

7. Multi-Channel Data from the Finger

The present disclosure has stressed the importance of stable skin/sensor contact. In particular, at least one embodiment of the disclosure is directed at retaining the sensor surface in contact with the skin of the third phalange, the traditional ring position on the finger. During the testing of the disclosed apparatus sensor data has been collected to determine if data obtained from the ring position of the finger is similar to that conventionally collected from a fingertip. It will be noted that the density of eccrine glands is greater at the fingertip so both positions were tested to compare.

Figure 15A:
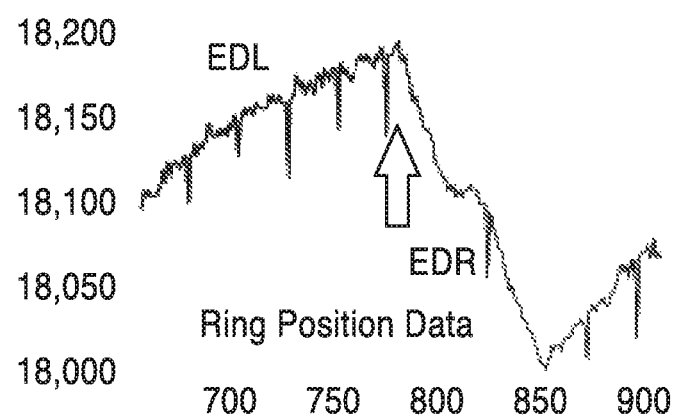
FIG. 15A and FIG. 15B are plots of EDA and PPG cardiac pulse obtained with a biometric sensing ring according to an embodiment of the present disclosure.
Figure 15B:
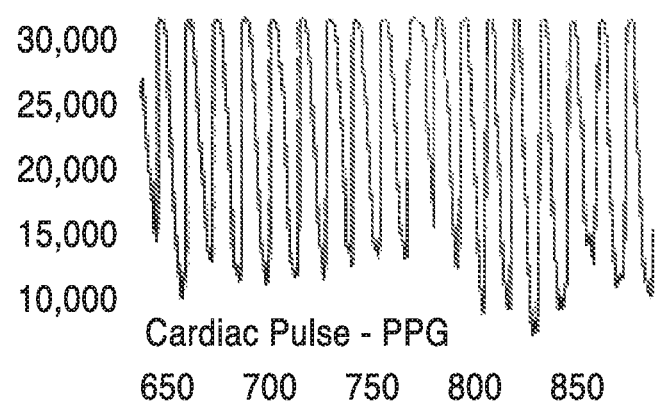
Figure 16A:
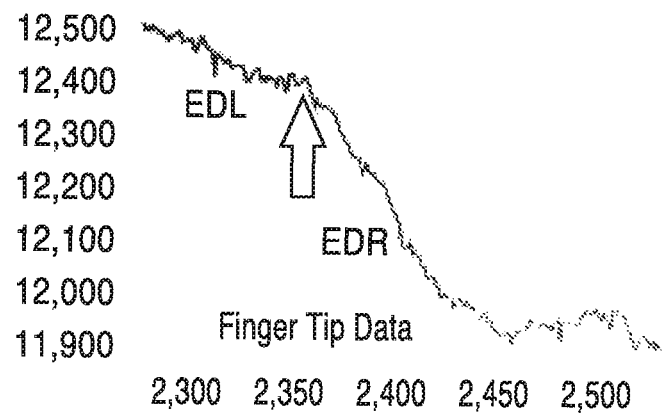
FIG. 16A and FIG. 16B are plots of EDA and PPG cardiac pulse obtained with a fingertip sensing device.
Figure 16B:
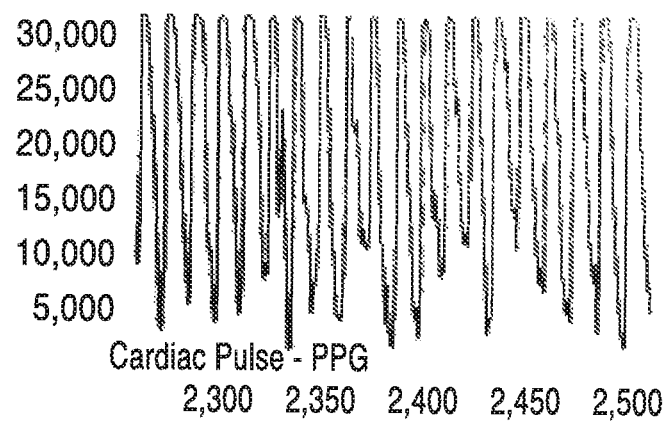

FIG. 15A through FIG. 16B provide comparisons between bio-metric sensing at the ring position, as seen in FIG. 15A and FIG. 15B, and at the fingertip as seen in FIG. 16A and FIG. 16B. In FIG. 15A and FIG. 16A, an EDA trace is shown, while in FIG. 15B and FIG. 16B a PPG cardiac pulse trace is depicted. It should be noted that the periodic spikes seen in FIG. 15A were caused by a low battery condition, and are not normally present in this EDA signal. The data is substantially similar between comparing the fingertip to the ring position.

However, as can be seen by the amplitude calibration on the vertical axes (arbitrary voltage units), the ring position EDR deflection (arrow) in FIG. 15A is lower in amplitude than the fingertip EDR deflection seen in FIG. 16A. These phasic responses were elicited by a sharp inhalation. The tonic level (EDL) is indicated as the section of the plot leading up to the phasic EDR deflection.

It should be noted that the above results were collected directly from the screen of a mobile device (i.e., Android based cellular phone running a bio-metric sensor data collection application) showing only a 15 second window. Additional detail is shown in a later section describing graphs for FIG. 21A through FIG. 23. Activation in FIG. 15A and FIG. 16A is indicated as a negative going deflection, however, in later figures the polarity is reversed to depict activation as positive going—which is perhaps more intuitive in that more stress equals a higher level on the graph. In addition, FIG. 15A through FIG. 16B do not depict the EDL context because the window is too small. The EDRs in FIG. 15A and FIG. 16B would appear similar to the EDR plot in the middle of FIG. 21A If a longer data record was shown. The PPG pulse data looks quite similar for both ring position and fingertip.

8. Flexible Circuit Board

The biometric sensor ring of the disclosure utilizes a distributed arrangement of sensors and/or circuitry interconnected using a flexible substrate interconnection, such as a flexible printed circuit. At least one embodiment fits all the necessary circuit components on the top and bottom of the ring, whereby a complete ring of flex board is not necessary. A two board solution was adopted in this form of embodiment between which is a narrow connecting flex section providing only signal and power lines connecting the two circuit sections.

Figure 17:
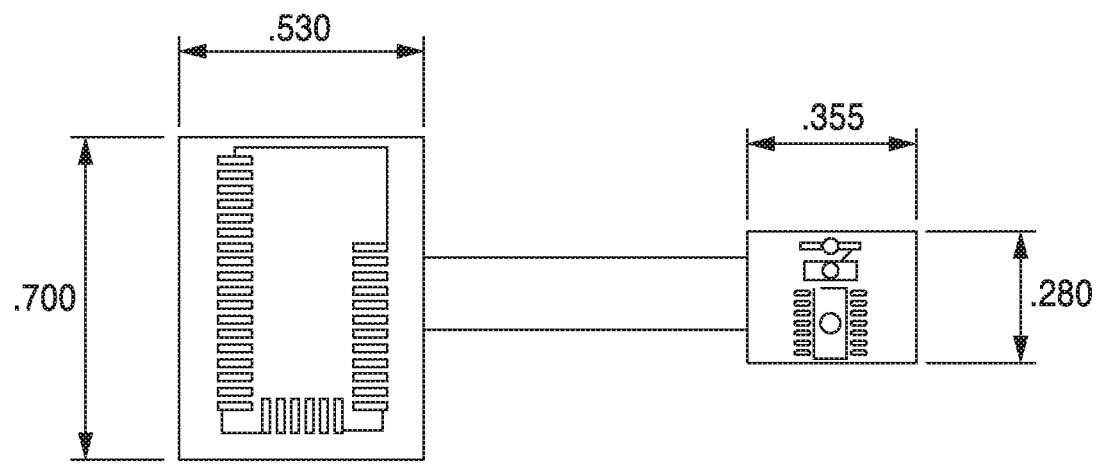
FIG. 17 and FIG. 18 are image renditions of both sides of a flex circuit within a biometric sensing ring according to an embodiment of the present disclosure.
Figure 18:
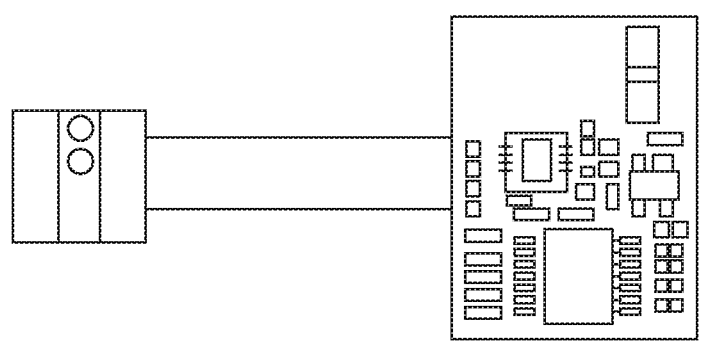

FIG. 17 and FIG. 18 illustrate an embodiment of the biometric sensing ring in which the circuitry is retained on two small circuit boards connected by a flex section containing the power and signal lines to and from the circuitry. The top surface of the circuit boards are shown as a rendition of an embodiment in FIG. 17. Similarly, the bottom surface of the circuit boards are shown as a rendition of an embodiment in FIG. 18.

In at least one embodiment, the main circuit board contains the Bluetooth low energy module (BLE) on one side (e.g., the left side in FIG. 17, and on the right side in FIG. 18. The two section flex board carries power and signal lines to/from the smaller sensor board (PPT and EDA1 and EDA2) that contacts the skin to the BLE circuitry. The smaller board also preferably contains a differential amplifier (QO) adjacent to the sensor elements for noise reduction purposes. The main circuit board contains the Bluetooth low energy module (BLE) on one side and the sensor circuit components on the other side. Several finger measurements were performed on different people, and an average was chosen for the overall length of the composite board at 1⅞ inches, with a narrow flex section of ⅞ inch. These dimensions span half the circumference of an average finger.

This embodiment of the design was formulated to position the BLE module on the top surface of the finger to optimize signal transmission without possible RF scattering effects caused by finger tissue. In addition, this embodiment places the EDA and PPG sensor elements on the bottom surface (palm side) of the finger for optimal biometric data acquisition.

Using the two section flex board, various ring configurations were implemented toward creating the most practical wearable device that could accommodate various finger sizes. A variety of ring designs were tested, such as using clay with internal wire frame and also of soft malleable plastic.

9. Wearable Design

In at least one embodiment, the ring configuration is in a "C" shaped design that is easy to slip on and off and accommodates different finger sizes, and has advantages over the closed ring design. The sensor board section is designed to contact the palm side of the finger. In this configuration, the battery is mounted under the sensor section. This "C" shaped structure places the sensor section firmly on the bottom of the finger, places the BLE module on top of the finger, and is comfortable for wearing over extended periods of time.

Figure 19:
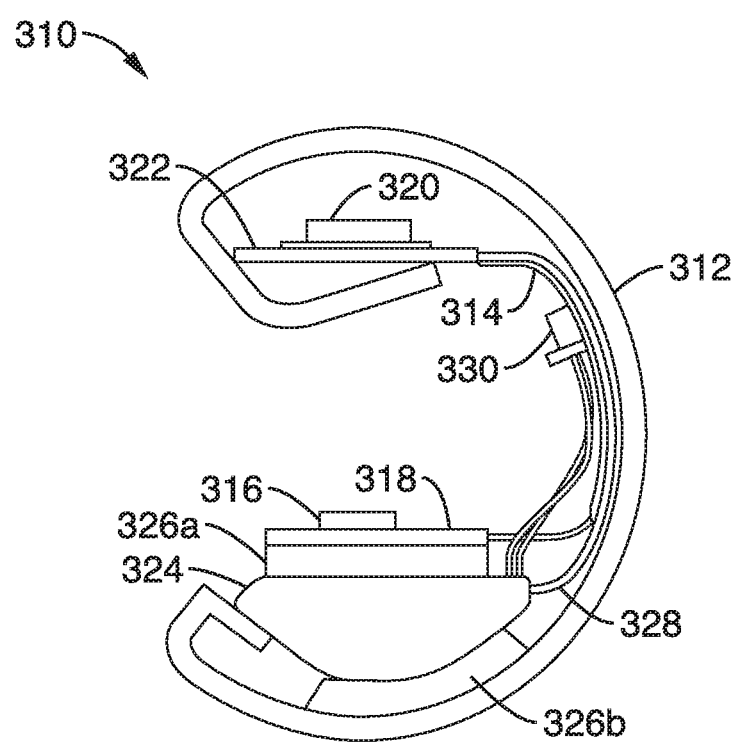
FIG. 19 is an image rendition of a "C" shaped biometric sensing ring according to an embodiment of the present disclosure.

FIG. 19 illustrates a "C" ring embodiment 310 shown in a prototype form with housing 312 made from ¾ inch wide InstaMorph® plastic. In FIG. 19, the flex circuit 314 is seen joining sensor circuitry 316 on a circuit board end 318 to a BLE circuit 320 on the opposing circuit board end 322. Battery 324 is seen sandwiched between adhesive foam sections 326a, 326b, with wiring 328 attaching to circuit board section 322. A recharging connector 330 is also shown to allow recharging the battery without removing it from the sensor ring.

In creating this housing 312, the InstaMorph plastic was prepared from pellets that were first dissolved in hot water and then formed into 1/16 inch thick sheets that could be cut into ¼ inch strips. A 3¼ inch strip of plastic was then formed into a "C" shape by re-softening the material in warm water. At the same time, a shelf was formed to hold the BLE section of the flexboard at the top, and a lip was formed at the bottom to retain the edge of the battery. The C ring has an outside diameter of 1¼ inches when not in use and can flex to an OD of 1¾ inches for larger fingers.

The C ring design also accommodates a rechargeable battery 324 that can power continuous data streaming for extended periods (e.g., 3 hours for a 700 mA-hour battery). It is expected that smaller form factors, and/or extended data collection times, can be achieved as more powerful batteries become available in the future. For data transmission reasons the battery is preferably not located on top of the BLE module, so this C ring embodiment locates the battery beneath the sensor section.

The C ring design yields high quality EDA and PPG data from a variety of users who have worn the ring on different fingers for data collection trials. The design places the sensor elements firmly on the skin to minimize motion artifact and yet is comfortable for long periods of wear.

Figure 20:
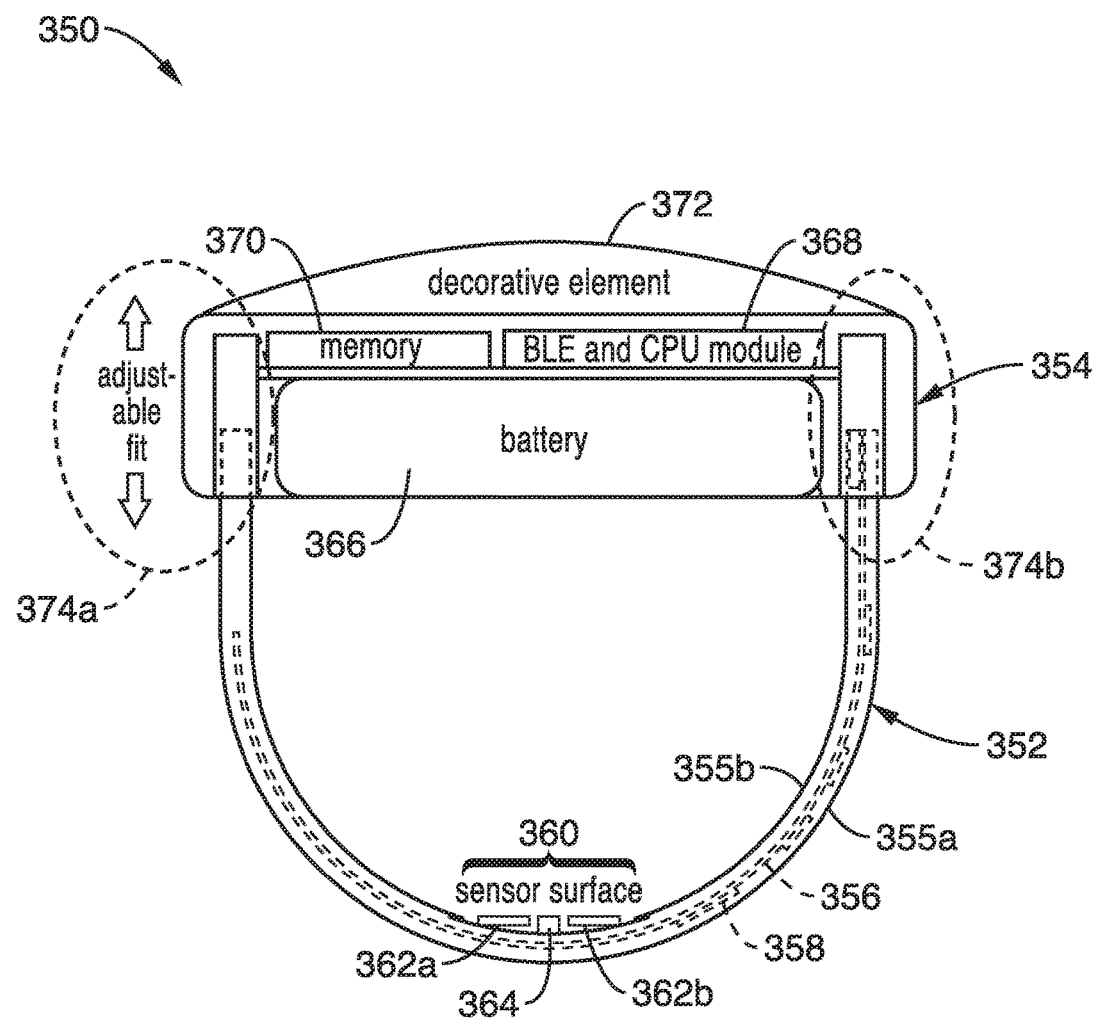
FIG. 20 is a side view of a "U" shaped biometric sensing ring according to an embodiment of the present disclosure, shown with battery and select circuits retained in a top portion which may be optionally adorned with a decorative element.

FIG. 20 illustrates an example embodiment 350 of a "U" shaped biometric sensor ring. In this embodiment, a "U" shaped lower portion 352 joins an upper disk portion 354 with a mechanism that allows one or both ends of the "U" shaped portion to be inserted to a desired depth so that the interior of the ring closes down on the finger sufficient to assure proper sensor contact on both the top and bottom surfaces of the finger. It will be noted that the top of the ring can be utilized for additional purposes, such as accommodating a fashion element 372, such as a jewel, or other decorative element, so that the sensor ring device can appear like a normal ring. It should also be appreciated that instead of (or along with) an ornamental structure (jewel), a small display interface can be integrated such as providing bio-sensing indicators, a clock, user input selectors (e.g., buttons), or other desired input/output functionality without departing from the teachings of the present disclosure.

Biometric sensing ring 350 has a lower portion 352 with exterior 355a, 355b, within which is retained a flex circuit 356 configured for mechanical and electrical connection to circuit devices (e.g., integrated circuits—"ICs") 358 and sensors 360, including EDA sensor inputs 362a, 362b, and other sensors 364. The sensors connect through flex circuit 356 with upper portion 354. It will be appreciated that if the embodiment is configured to allow both sides of the "U" shaped section to engage the top section at a variable depth, then a contact within the upper portion provides secure electrical connection along the engagement path.

The battery 366 is retained in the upper shoulder/setting portion 354 of the ring, thus streamlining the backside (band portion) of the ring keeping it small and comfortable for extended wear. In addition, the large circuit element of the BLE 368 is preferably located in this upper shoulder/setting portion 354 due to the larger size of the integrated circuit and also to provide clear signal output and reception. It will be noted that the CPU for controlling the sensing ring, may be integrated with the BLE (e.g., use its same computer processor). Otherwise, a CPU may be incorporated which is separate from the BLE as desired. In addition a memory circuit 370 is shown which couples to the BLE/CPU, and is preferably located in this upper shoulder/setting portion 354. In at least one embodiment, the battery is configured for being readily removed, and inserted from the ring, such as to allow insertion of a charged battery while charging the first one. The replaceable battery allows continuous data collection use from a power perspective. In addition, different battery sizes can be utilized depending on the use case. Multiple user interaction features and/or fashion statement possibilities are also supported by this upper shoulder/setting portion of the sensor ring.

The adjustability of the fit is seen for moving at least one end of the "U" shaped portion 352 in and out of the top portion 354. In at least one embodiment, side 374b is fixed simplifying the connection of the flex circuit 356 to the circuit module containing battery 366, memory 370, and the CPU and BLE 368 circuits. The adjustable engagement 374a can be implemented in various ways, such as ratchet steps and corresponding detents whereby the "U" shaped portion 352 is manually snapped into the desired position into the top portion 354. In certain embodiments, a release mechanism is configured so that engagement can be tightened by pressing "U" shaped portion 352 further into the top portion 352, but requiring the release to be activated to loosen the fit. Many release mechanisms are known, such as may be activated by applying pressure to one or more locations in the top portion 354, such as across its diameter, or compression of the top of the "U" shaped portion 352 near where it joins top portion 352.

10. Ring Data and Smart Phone Apps

The biometric sensor ring is configured to send sensor data to the mobile device, such as through the BLE interface, to be decoded in the mobile device application that can: (a) display information in a raw data form (e.g., graphing routine); (b) analyze (process) the information and display average values, time related values, threshold related values, emotional state charts/plots/indicators; (c) displaying animations to depict the raw and/or analyzed sensor information; (d) utilize the raw and/or analyzed data within a game or other application utilizing the emotional estimations as part of its received information (e.g., application may also take inputs from keyboards, pointing devices, mobile device motion sensing, mobile device position (i.e., GPS), etc.).

It should be appreciated that the decoding includes decoding from format utilized in the wireless communication protocol, such as BlueTooth, and putting the signal in a format, including any desired scaling or offset, to simplify data display and any calculations performed interoperatively on the data signals as a whole. These software routines are executed on the processor of the mobile device.

Raw data can be derived and displayed by the mobile device sensor ring application using information collected from multiple sensor feedback channels. By way of example and not limitation, these channels comprise: (1) EDR tonic, (2) EDR phasic, (3) infrared (IR) reflection (cardiac pulse), (4) skin temperature, (5) chemical sensing, (6) acceleration sensing in X, Y, and Z directions. Additional information is provided in response to processing performed on the raw data, which is particularly useful for various interactive applications, which may be created for running on the mobile phone, or in certain embodiments, for limited display/annunciation on the biometric sensor ring itself.

The system of the present disclosure derives emotion metrics from the data collected by the biometric sensing ring, which include heart rate (HR), heart rate variability (HRV), and respiration rate based on HRV, as well as activity information on an acceleration sensor.

Accelerations sensed by the acceleration sensor are utilized for correlating activity with stress conditions. For example a heart rate increase is expected when one is moving, such as running or walking rapidly, but indicates something quite different if one is seated talking on a telephone.

In addition, the acceleration information is utilized in at least one embodiment for artifact rejection in the EDA and/or PPG sense data. By way of example and not limitation, two modes of biometric sensor artifact rejection are described below which utilize temporal correlation between the signal to the corrected and the accelerometer signals. It will be noted that the signals to be corrected are low frequency signals (e.g., EDA is in the range from 0.25 Hz to 5 Hz), while the motion artifacts contain higher frequency content, such as at and above approximately 20 Hz to 100 Hz.

By way of example and not limitation, the following exemplifies correcting the EDR and PPG signal. In the first mode, the EDA and PPG data is rejected in response to sensing a sufficient acceleration (e.g., exceeding a motion threshold) from the acceleration sensor, thus eliminating the section of signal containing the motion artifact. This mode can also preferably verify that the EDA and/or PPG data signal contains high frequency content prior to eliminating that section of the signal being registered. The program simply shuts off EDA and PPG channel data when a high frequency EDA signal input comes at the same time as a sufficient acceleration is sensed in either X, Y, or Z directions to cross a desired amplitude threshold. This may be performed, by way of example, by electrically blocking the signal or removing representative data entries from a buffer. The interrupt in the EDA and PPG signals only lasts as long as the motion artifact, whereby the output signals are restored when either acceleration or high frequency EDA and/or PPG signals return to their normal low frequency nature.

In the second mode, a form of noise cancelation is provided. This noise cancelation form of correction requires more processing overhead than the first mode of correction. In response to receiving a sufficient acceleration (e.g., exceeding a motion threshold), and preferably also detecting a high frequency component in the EDA and/or PPG signal, then a compensation signal representing the motion artifact is subtracted from the EDA and/or PPG signals. The compensation signal can be determined from the acceleration signals, or from the high-frequency components of the EDA or PPG signal being corrected, or more preferably to a combination of acceleration and EDA/PPG signals. As a result of this form of cancelation, only the motion artifact is removed from the corrected EDA and/or PPG signals. In one embodiment, the compensation signal is generated on a parallel channel and has a component which is 180 degrees out of phase with the motion artifact contained in the EDA and/or PPG signal. The generated EDA and/or PPG signal is then combined with the compensation signal to generate a corrected EDA and/or PPG signal without the motion artifacts.

The above data analysis is given by way of example and not limitation, as one of ordinary skill in the art will appreciate that numerous methods are known for processing biometric information into estimations of emotional state, any of which (and combinations thereof) may be programmed into the biometric sensing ring system of the present disclosure without departing from the teachings disclosed herein.

Figure 21A:
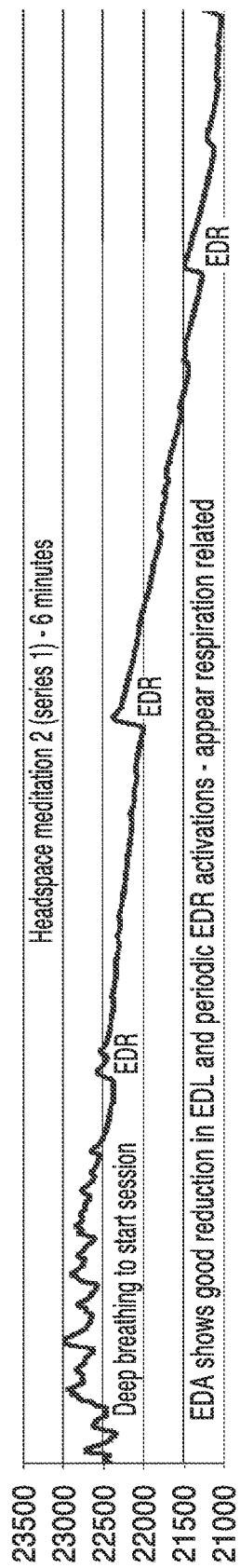
FIG. 21A through FIG. 23 are plots of biometric information collected by a biometric sensing ring according to an embodiment of the present disclosure.
Figure 21B:
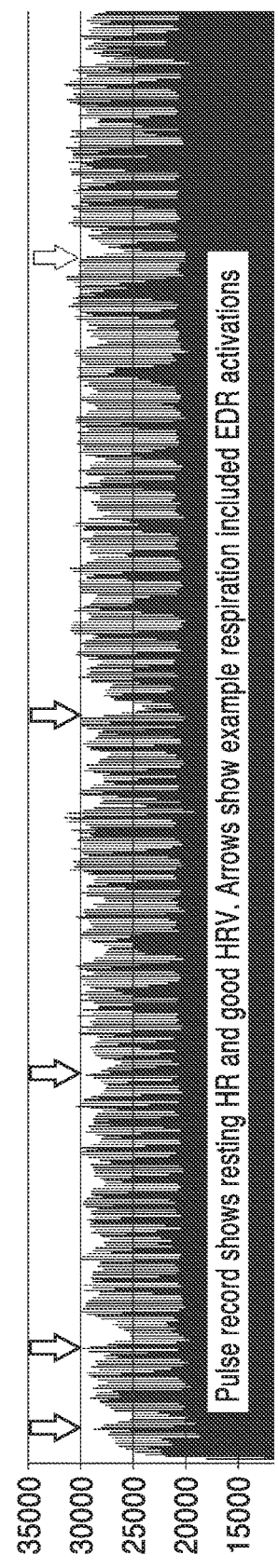
Figure 22A:
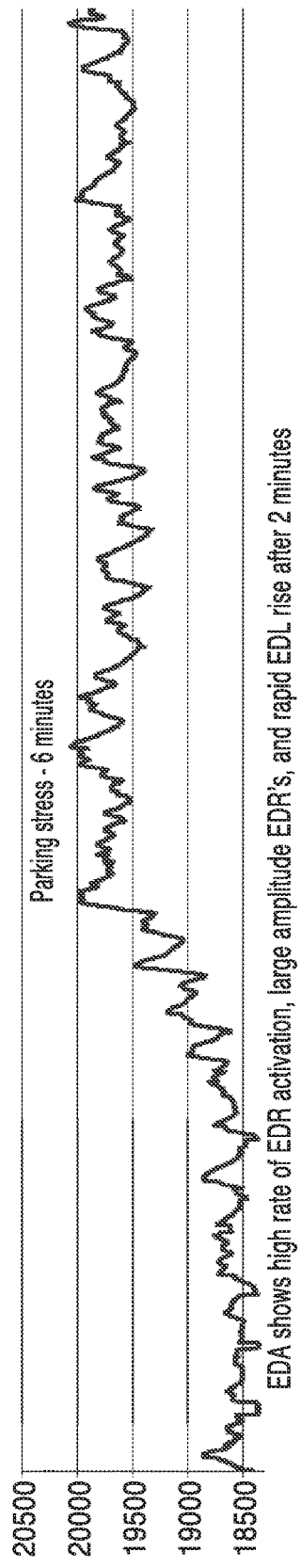
Figure 22B:
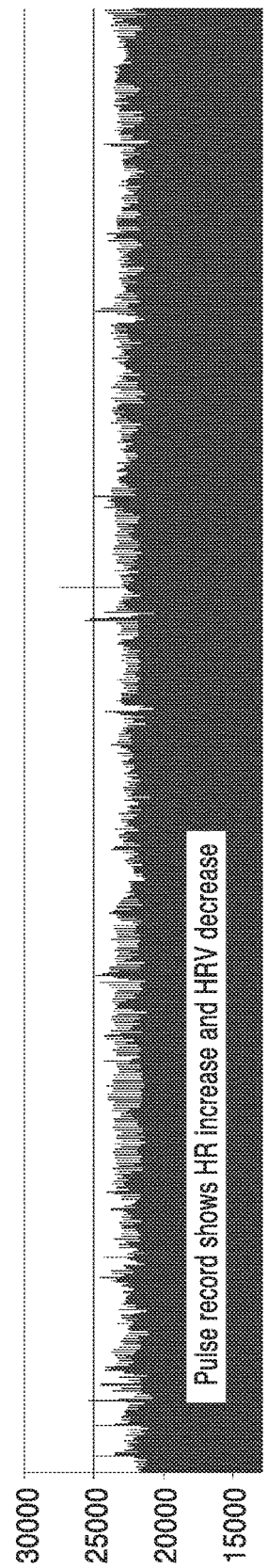
Figure 23:
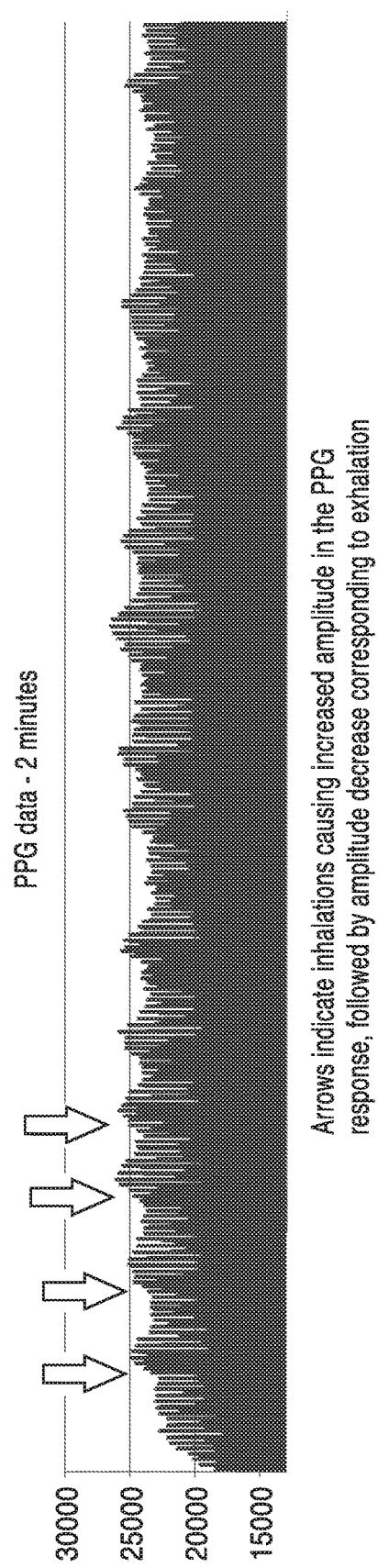

FIG. 21A through FIG. 23 depict data recording examples made possible with the ring biometrics. In FIG. 21A, EDA data is seen showing results during headspace meditation over a period of 6 minutes, with a session of deep breathing initiating the session. A reduction in EDA is seen over the 6 minute test. In FIG. 21B a pulse record is seen associated with the headspace meditation test, which shows a good resting HR and HRV. In FIG. 22A, EDA data is seen over a 6 minute collection period during vehicle parking, illustrating "parking stress" showing a high rate of EDR activation, large amplitude EDR's and rapid EDL rise after 2 minutes, with FIG. 22B showing a corresponding pulse record with HR increase and HRV decrease. In FIG. 23 is seen PPG data over a 2 minute period with arrows indicating inhalations causing increased amplitude in the PPG response followed by amplitude decrease corresponding to exhalations.

As mentioned previously, the highest resolution EDA and PPG data is obtained from readings taken at the fingers. In one of many possible use cases, this biometric data allows people to monitor and manage their stress levels. Sympathetic nervous system (SNS) activation as indicated by specific EDA and PPG features are detectable by the ring. No one biometric feature is sufficient to categorize stress or other user emotions. A combination of biometric signals is necessary to categorize user state. In the case of stress and relaxation monitoring, five biometric features are used here as indicators: EDR rate, EDR amplitude, $\Delta$EDL over 3-5 minutes, HR, and HRV.

The first example illustrated by FIG. 22A and FIG. 22B shows six minutes of raw EDA and PPG data plotted to demonstrate the change in biometric levels while meditating. "Headspace" is a consumer app that provides narration for a meditation session. In this example, some EDR activations can be seen at the beginning of the session corresponding to several deep breaths, then a long progressive decrease in the EDL accompanied by a very low EDR rate (less than 1 per minute). The PPG data shows a slightly decreasing HR and slight increase in HRV (derived, not visible in the raw data). The combination of these features indicates a good level of relaxation induced by this meditation exercise. Another interesting feature of the raw PPG data is the varying amplitude of the IR sensor response. This variation approximately corresponds to respiration rate. The arrows in FIG. 22B indicate the PPG amplitude deflections that correspond to deeper inhalations from the user.

In the second example illustrated by FIG. 23A and FIG. 23B, data was recorded while a driver was looking for parking in San Francisco, Calif. which is known for both its beauty and its parking problems. This record shows high amplitude EDRs evoked at a high rate (up to 12 per minute) with a rapid increase in EDL between minutes 2 and 3. The PPG shows increased HR and decreased HRV in this period. Taken together, these features indicate a high level of sustained stress. Sustained stress is indicated by the increase in EDL to a maximum (plateau) with continued high EDR rate.

The respiratory rhythm visible in the PPG data enables utilizing a novel method to derive user respiration rate. If the user is sitting quietly, the respiratory periodicity can be seen in the raw data as illustrated in FIG. 24. With motion artifact filtering, respiration rate can be derived from the PPG data when the user is engaged in physical movement.

Embodiments of the present technology may be described with reference to flowchart illustrations of methods and systems according to embodiments of the technology, and/or algorithms, formulae, or other computational depictions, which may also be implemented as computer program products. In this regard, each block or step of a flowchart, and combinations of blocks (and/or steps) in a flowchart, algorithm, formula, or computational depiction can be implemented by various means, such as hardware, firmware, and/or software including one or more computer program instructions embodied in computer-readable program code logic. As will be appreciated, any such computer program instructions may be loaded onto a computer, including without limitation a general purpose computer or special purpose computer, or other programmable processing apparatus to produce a machine, such that the computer program instructions which execute on the computer or other programmable processing apparatus create means for implementing the functions specified in the block(s) of the flowchart(s).

Accordingly, blocks of the flowcharts, algorithms, formulae, or computational depictions support combinations of means for performing the specified functions, combinations of steps for performing the specified functions, and computer program instructions, such as embodied in computer-readable program code logic means, for performing the specified functions. It will also be understood that each block of the flowchart illustrations, algorithms, formulae, or computational depictions and combinations thereof described herein, can be implemented by special purpose hardware-based computer systems which perform the specified functions or steps, or combinations of special purpose hardware and computer-readable program code logic means.

Furthermore, these computer program instructions, such as embodied in computer-readable program code logic, may also be stored in a computer-readable memory that can direct a computer or other programmable processing apparatus to function in a particular manner, such that the instructions stored in the computer-readable memory produce an article of manufacture including instruction means which implement the function specified in the block(s) of the flowchart(s). The computer program instructions may also be loaded onto a computer or other programmable processing apparatus to cause a series of operational steps to be performed on the computer or other programmable processing apparatus to produce a computer-implemented process such that the instructions which execute on the computer or other programmable processing apparatus provide steps for implementing the functions specified in the block(s) of the flowchart(s), algorithm(s), formula(e), or computational depiction(s).

It will further be appreciated that the terms "programming" or "program executable" as used herein refer to one or more instructions that can be executed by a processor to perform a function as described herein. The instructions can be embodied in software, in firmware, or in a combination of software and firmware. The instructions can be stored local to the device in non-transitory media, or can be stored remotely such as on a server, or all or a portion of the instructions can be stored locally and remotely. Instructions stored remotely can be downloaded (pushed) to the device by user initiation, or automatically based on one or more factors. It will further be appreciated that as used herein, that the terms processor, computer processor, central processing unit (CPU), and computer are used synonymously to denote a device capable of executing the instructions and communicating with input/output interfaces and/or peripheral devices.

From the description herein, it will be appreciated that that the present disclosure encompasses multiple embodiments which include, but are not limited to, the following:

1. A biometric sensing ring apparatus for estimating emotional state of a user for display on a mobile device, said apparatus comprising: (a) at least one biometric sensing ring configured for wearing on the finger, or fingers, of a user over extended periods while the user performs their normal activities; (b) a plurality of sensors retained in a housing of said biometric sensing ring to extend into its interior for establishing secure skin contact on a portion of the finger of the user while the biometric sensing ring is being worn; (c) wherein said plurality of sensors comprise an electrodermal response (EDA), photoplethysmograph (PPG), temperature; (d) an acceleration sensor configured for sensing accelerations in three dimensions as the user performs their activities; (e) a control circuit configured for collecting biometric information from said plurality of sensors and said acceleration sensor, for storage in a memory and for communication to a mobile device; (f) a power storage device retained in said biometric sensing ring for supplying power to said plurality of sensors, said acceleration sensor, and said control circuit; and (g) a communications interface coupled to, or integrated with, said control circuit, said communications interface configured for communicating data from said biometric sensing ring to a mobile device having an application program configured for displaying estimated emotional state of a user.

2. The apparatus of any preceding embodiment, wherein said mobile device is configured for analyzing biometric information and displaying the results of the analysis.

3. The apparatus of any preceding embodiment, wherein said communications interface comprises a low power Bluetooth communications circuit for performing low power RF communication between said biometric sensing ring and the mobile device.

4. The apparatus of any preceding embodiment, further comprising a flexible circuit board retained within a portion of the biometric sensing ring, wherein said flexible circuit board electrically interconnects said power storage device, said plurality of sensors, and said accelerometer with said control circuit.

5. The apparatus of any preceding embodiment, wherein said flexible circuit board is disposed around at least one half of the periphery of said biometric sensing ring to interconnect sensors configured for sensing the underside of the user's fingers, with sensors configured for sensing the upper side of the user's finger.

6. The apparatus of any preceding embodiment, wherein a housing of said biometric sensing ring is configured with a variable geometry for retaining said plurality of sensors at a desired mechanical contact pressure on the skin of the finger upon which the biometric sensing ring is being worn.

7. The apparatus of any preceding embodiment, wherein said mechanical contact pressure is generated by said biometric sensing ring as selected from the group of mechanical pressure application means consisting of a biasing member, a malleable material in said housing, a detent position engagement structure, an expanding memory foam, a pneumatic expansion structure, and combinations thereof.

8. The apparatus of any preceding embodiment, further comprising a top housing extending from the upper portion of the biometric sensing ring and configured for retaining said power storage device and selected circuitry.

9. The apparatus of any preceding embodiment, wherein said EDA sensor generates a tonic signal and a phasic signal as an indication of arousal and mood.

10. The apparatus of any preceding embodiment, wherein said PPG sensor measures user cardiac pulse from which heart rate (HR), heart rate variability (HRV) and respiratory rate are determined.

11. The apparatus of any preceding embodiment, wherein said plurality of sensors further comprises a chemical sensor configured for detecting certain chemical levels in user sweat.

12. The apparatus of any preceding embodiment, wherein said chemicals being detected by said chemical sensor are selected from the group of chemicals consisting of blood sugar, cortisol, and metabolic products from drugs or hormones.

13. The apparatus of any preceding embodiment, wherein said chemical sensor is mounted on the top interior of the ring for retention upon the upper side of the user's finger.

14. The apparatus of any preceding embodiment, wherein said power storage device retained in said biometric sensing ring makes said biometric sensing ring self-contained so that the user is not tethered by external electrical connections that could hamper their normal activities.

15. The apparatus of any preceding embodiment, wherein said at least one biometric sensing ring comprises multiple interconnected electronic biometric sensing rings worn on a single finger of the user, or on different fingers, or a combination with rings on multiple fingers and at least one finger having more than one ring.

16. The apparatus of any preceding embodiment, wherein said at least one biometric sensing ring comprises multiple biometric sensing rings integrated within a biometric sensing glove to be worn over the hand of the user whose fingers are disposed within said multiple biometric sensing rings.

17. A biometric sensing ring apparatus for estimating emotional state of a user for display on a mobile device, said apparatus comprising: (a) at least one biometric sensing ring configured for wearing on the finger, or fingers, of a user over extended periods while the user performs their normal activities; (b) a plurality of sensors retained in a housing of said biometric sensing ring to extend into its interior for establishing secure skin contact on a portion of the finger of the user while the biometric sensing ring is being worn; (c) wherein said plurality of sensors comprise an electrodermal response (EDA), photoplethysmograph (PPG), temperature; and (d) wherein said EDR sensor generates a tonic signal and a phasic signal as an indication of arousal and mood, and said PPG sensor measures user cardiac pulse from which heart rate (HR), heart rate variability (HRV), and respiratory rate are determined; (e) an acceleration sensor configured for sensing accelerations in three dimensions as the user performs their activities; (f) a housing of said biometric sensing ring configured with a variable geometry for retaining said plurality of sensors at a desired mechanical contact pressure on the skin of a finger upon which the biometric sensing ring is being worn; (g) a control circuit configured for collecting biometric information collected from said plurality of sensors and said acceleration sensor for storage in a memory and for communication to a mobile device; (h) a power storage device retained in said biometric sensing ring for supplying power to said plurality of sensors, said acceleration sensor, and said control circuit; and (i) a communications interface coupled to, or integrated with, said control circuit, said communications interface configured for communicating data from said biometric sensing ring to a mobile device having an application program configured for displaying estimated emotional state of a user.

18. The apparatus of any preceding embodiment, wherein said mechanical contact pressure is generated by said biometric sensing ring as selected from the group of mechanical pressure application means consisting of a biasing member, a malleable material in said housing, a detent position engagement structure, an expanding memory foam, a pneumatic expansion structure, and combinations thereof.

19. The apparatus of any preceding embodiment, further comprising a flexible circuit board retained within a portion of the biometric sensing ring spanning at least one half of its periphery, with said flexible circuit board electrically interconnecting said power storage device, said plurality of sensors, and said accelerometer with said control circuit.

20. The apparatus of any preceding embodiment, further comprising a top housing extending from the upper portion of the biometric sensing ring and configured for retaining said power storage device and selected circuitry.

21. The apparatus of any preceding embodiment, wherein said plurality of sensors further comprises a chemical sensor configured for detecting certain chemical levels in user sweat.

22. The apparatus of any preceding embodiment, wherein said chemicals being detected by said chemical sensor are selected from the group of chemicals consisting of blood sugar, cortisol, and metabolic products from drugs or hormones.

23. The apparatus of any preceding embodiment, wherein said chemical sensor is mounted on the top interior of the ring for retention upon the upper side of the user's finger.

24. The apparatus of any preceding embodiment, wherein said power storage device retained in said biometric sensing ring makes said biometric sensing ring self-contained so that the user is not tethered by external electrical connections that could hamper their normal activities.

25. The apparatus of any preceding embodiment, wherein said at least one biometric sensing ring comprises multiple interconnected electronic biometric sensing rings worn on a single finger of the user, or on different fingers, or a combination with rings on multiple fingers and at least one finger having more than one ring.

26. The apparatus of any preceding embodiment, wherein said at least one biometric sensing ring comprises multiple biometric sensing rings integrated within a biometric sensing glove to be worn over the hand of the user whose fingers are disposed within said multiple biometric sensing rings.

27. A biometric sensing ring apparatus for estimating emotional state of a user for display on a mobile device, said apparatus comprising: (a) at least one biometric sensing ring configured for wearing on the finger, or fingers, of a user over extended periods while the user performs their normal activities; (b) a housing of said biometric sensing ring having an upper shoulder/setting portion of the housing and a lower band portion of the housing; (c) a plurality of bio-sensors retained in the lower band portion of the housing facing upward into a ring finger-hole interior area for establishing secure skin contact on a portion of the finger of the user while the biometric sensing ring is being worn; (d) wherein said plurality of bio-sensors comprise an electrodermal response (EDA), photoplethysmograph (PPG), temperature; (e) an acceleration sensor configured for sensing accelerations in three dimensions as the user performs their activities; (f) a control circuit configured for collecting biometric information from said plurality of bio-sensors and said acceleration sensor, for storage in a memory and for communication to a mobile device; (g) a power storage device retained in said upper shoulder/setting portion of the housing for supplying power to said plurality of sensors, said acceleration sensor, and said control circuit; and (h) a communications interface retained in said upper shoulder/setting portion of the housing and coupled to, or integrated with, said control circuit, wherein said communications interface is configured for communicating data from said biometric sensing ring to a mobile device having an application program configured for displaying estimated emotional state of a user; (i) wherein said upper shoulder/setting portion of the housing is configured with an adjustable connection depth interface with said lower band, whereby the sizing of the ring and thus contact pressure with said plurality of bio-sensors is controlled in response to adjusting this connection depth; and (j) wherein said plurality of bio-sensors are connected on a flexible circuit which extends from an area of said lower band on up to make electrical connection with circuitry within said upper shoulder/setting portion of the housing.

28. The apparatus of any preceding embodiment, wherein a top surface of said upper shoulder/setting portion of the housing is configured for receiving one or more elements selected from the group of elements consisting of decorative elements, display indicators, and user input selectors.

29. The apparatus of any preceding embodiment, wherein said battery is configured for being readily removed, so that another battery can be reinserted to increase time periods over which biometric data is collected by said biometric sensing ring apparatus.

30. The apparatus of any preceding embodiment, wherein said plurality of sensors further comprise a chemical sensor configured for detecting certain chemical levels in user sweat.

Although the description herein contains many details, these should not be construed as limiting the scope of the disclosure but as merely providing illustrations of some of the presently preferred embodiments. Therefore, it will be appreciated that the scope of the disclosure fully encompasses other embodiments which may become obvious to those skilled in the art.

In the claims, reference to an element in the singular is not intended to mean "one and only one" unless explicitly so stated, but rather "one or more." All structural, chemical, and functional equivalents to the elements of the disclosed embodiments that are known to those of ordinary skill in the art are expressly incorporated herein by reference and are intended to be encompassed by the present claims. Furthermore, no element, component, or method step in the present disclosure is intended to be dedicated to the public regardless of whether the element, component, or method step is explicitly recited in the claims. No claim element herein is to be construed as a "means plus function" element unless the element is expressly recited using the phrase "means for". No claim element herein is to be construed as a "step plus function" element unless the element is expressly recited using the phrase "step for".

What is claimed is:

1. A biometric sensing ring apparatus for estimating emotional state of a user for display on a mobile device, said apparatus comprising:

a biometric sensing ring configured for wearing on the finger of the user over extended periods while allowing the user to perform normal activities;

a housing of said biometric sensing ring, wherein said housing comprises an upper shoulder/setting portion of the housing configured for retaining a power storage device, and a lower band portion of the housing which is "U" shaped;

wherein said upper shoulder/setting portion is configured for receiving ends of said "U" shaped lower band portion so that one or both ends of this "U" shaped lower band portion are inserted to a desired depth into said upper shoulder/setting portion so that the interior of the ring closes down on the finger sufficient to assure proper sensor contact on both the top and bottom surfaces of the finger;

a plurality of sensors retained in said housing of said biometric sensing ring to extend into its interior for establishing secure skin contact on a portion of the finger of the user while the biometric sensing ring is being worn;

wherein said plurality of sensors comprise an electrodermal activity (EDA), photoplethysmograph (PPG), temperature;

an acceleration sensor configured for sensing accelerations in three dimensions as the user performs normal activities;

a control circuit configured for collecting biometric information from said plurality of sensors and said acceleration sensor, for storage in a memory and for communication to the mobile device;

wherein said power storage device is configured for supplying power to said plurality of sensors, said acceleration sensor, and said control circuit; and a communications interface coupled to, or integrated with, said control circuit, said communications interface configured for communicating data from said biometric sensing ring to the mobile device having an application program configured for displaying estimated emotional state of the user;

wherein a flexible circuit board is retained within said lower band portion of the biometric sensing ring, wherein said flexible circuit board electrically interconnects sensors within said plurality of sensors;

wherein said flexible circuit board is disposed around at least one half of the periphery of said biometric sensing ring to interconnect sensors configured for sensing the underside of the user's finger, with sensors configured for sensing the upper side of the user's finger; and wherein said flexible circuit is configured for retaining circuit elements distributed along said flexible circuit board and flex spaces between said circuit elements.

2. The apparatus as recited in claim 1, wherein the mobile device is configured for analyzing biometric information and displaying the results of the analysis.

3. The apparatus as recited in claim 1, wherein said communications interface comprises a low power a Bluetooth communications circuit for performing low power radio frequency (RF) communication between said biometric sensing ring and the mobile device.

4. The apparatus as recited in claim 1, wherein at least one of the ends of said "U" shaped lower band portion is configured to electrically connect said circuit elements on said flexible circuit to said upper shoulder/setting portion.

5. The apparatus as recited in claim 1, wherein said communications interface is retained in said upper shoulder/setting disk portion of said biometric sensing ring and coupled to, or integrated with, said control circuit, wherein said communications interface is configured for communicating data from said biometric sensing ring to the mobile device having an application program configured for displaying estimated emotional state of the user.

6. The apparatus as recited in claim 1, wherein said EDA sensor generates a tonic signal and a phasic signal as an indication of arousal and mood.

7. The apparatus as recited in claim 1, wherein said PPG sensor measures user cardiac pulse from which heart rate (HR), heart rate variability (HRV) and respiratory rate are determined.

8. The apparatus as recited in claim 1, wherein said plurality of sensors further comprises a chemical sensor configured for detecting certain chemical levels in user sweat.

9. The apparatus as recited in claim 8, wherein said chemicals being detected by said chemical sensor are selected from the group of chemicals consisting of blood sugar, cortisol, and metabolic products from drugs or hormones.

10. The apparatus as recited in claim 8, wherein said chemical sensor is mounted on the top interior of the ring for retention upon the upper side of the user's finger.

11. The apparatus as recited in claim 1, wherein said power storage device retained in said biometric sensing ring makes said biometric sensing ring self-contained so that the user is not tethered by external electrical connections that could hamper normal activities.

12. The apparatus as recited in claim 1, wherein said biometric sensing ring is configured for interconnecting multiple biometric sensing rings worn on a single finger of the user, or on different fingers of the user, or a combination with rings on multiple fingers and at least one finger having more than one ring.

13. The apparatus as recited in claim 12, wherein said multiple biometric sensing rings are configured for integration within a biometric sensing glove to be worn over the hand of the user whose fingers are disposed within said multiple biometric sensing rings.

14. A biometric sensing ring apparatus for estimating emotional state of a user for display on a mobile device, said apparatus comprising:
a biometric sensing ring configured for wearing on the finger of the user over extended periods while allowing the user to perform normal activities;
a housing of said biometric sensing ring, wherein said housing comprises an upper shoulder/setting portion of the housing configured for retaining a power storage device, and a lower band portion of the housing which is "U" shaped;
wherein said upper shoulder/setting portion is configured for receiving ends of said "U" shaped lower band portion so that one or both ends of this "U" shaped lower band portion are inserted to a desired depth into said upper shoulder/setting portion so that the interior of the ring closes down on the finger sufficient to assure proper sensor contact on both the top and bottom surfaces of the finger;
a plurality of sensors retained in said housing of said biometric sensing ring to extend into its interior for establishing secure skin contact on a portion of the finger of the user while the biometric sensing ring is being worn;
wherein said plurality of sensors comprise an electrodermal activity (EDA), photoplethysmograph (PPG), temperature;
wherein said EDA sensor generates a tonic signal and a phasic signal as an indication of arousal and mood, and said PPG sensor measures user cardiac pulse from which heart rate (HR), heart rate variability (HRV), and respiratory rate are determined;
an acceleration sensor configured for sensing accelerations in three dimensions as the user performs their activities;
a housing of said biometric sensing ring configured with a variable geometry for retaining said plurality of sensors at a desired mechanical contact pressure on the skin of a finger upon which the biometric sensing ring is being worn;
a control circuit configured for collecting biometric information collected from said plurality of sensors and said acceleration sensor for storage in a memory and for communication to the mobile device;
wherein said power storage device is configured for supplying power to said plurality of sensors, said acceleration sensor, and said control circuit; and
a communications interface coupled to, or integrated with, said control circuit, said communications interface configured for communicating data from said biometric sensing ring to the mobile device having an application program configured for displaying estimated emotional state of a user;
wherein a flexible circuit board is retained within said lower band portion of the biometric sensing ring spanning at least one half of its periphery, with said flexible circuit board electrically interconnecting sensors within said plurality of sensors; and
wherein said flexible circuit is configured for retaining circuit elements distributed along said flexible circuit board and flex spaces between the components.

15. The apparatus as recited in claim 14, wherein at least one of the ends of said "U" shaped lower band portion is configured to electrically connect said circuit elements on said flexible circuit to said upper shoulder/setting portion.

16. The apparatus as recited in claim 14, wherein said plurality of sensors further comprises a chemical sensor configured for detecting certain chemical levels in user sweat.

17. The apparatus as recited in claim 16, wherein said chemicals being detected by said chemical sensor are selected from the group of chemicals consisting of blood sugar, cortisol, and metabolic products from drugs or hormones.

18. The apparatus as recited in claim 16, wherein said chemical sensor is mounted on the top interior of the ring for retention upon the upper side of the user's finger.

19. The apparatus as recited in claim 14, wherein said power storage device retained in said biometric sensing ring makes said biometric sensing ring self-contained so that the user is not tethered by external electrical connections that could hamper normal activities.

20. The apparatus as recited in claim 14, wherein said biometric sensing ring is configured for interconnecting multiple biometric sensing rings worn on a single finger of the user, or on different fingers of the user, or a combination with rings on multiple fingers and at least one finger having more than one ring.

21. The apparatus as recited in claim 20, wherein said multiple biometric sensing rings are configured for integration within a biometric sensing glove to be worn over the hand of the user whose fingers are disposed within said multiple biometric sensing rings.

22. A biometric sensing ring apparatus for estimating emotional state of a user for display on a mobile device, said apparatus comprising:
- a biometric sensing ring configured for wearing on the finger of the user over extended periods while the user performs their normal activities;
- a housing of said biometric sensing ring having an upper shoulder/setting portion of the housing and a lower band portion of the housing;
- wherein said upper shoulder/setting portion of the housing is configured for retaining a power storage device, and a lower band portion of the housing is "U" shaped;
- a plurality of bio-sensors retained in the lower band portion of the housing facing upward into a ring finger-hole interior area for establishing secure skin contact on a portion of the finger of the user while the biometric sensing ring is being worn;
- wherein said plurality of bio-sensors comprise an electrodermal response (EDA), photoplethysmograph (PPG), temperature;
- an acceleration sensor configured for sensing accelerations in three dimensions as the user performs normal activities;
- a control circuit configured for collecting biometric information from said plurality of bio-sensors and said acceleration sensor, for storage in a memory and for communication to the mobile device;
- wherein said power storage device is configured for supplying power to said plurality of sensors, said acceleration sensor, and said control circuit; and
- a communications interface retained in said upper shoulder/setting portion of the housing and coupled to, or integrated with, said control circuit, wherein said communications interface is configured for communicating data from said biometric sensing ring to the mobile device having an application program configured for displaying estimated emotional state of the user;
- wherein said upper shoulder/setting portion is configured for receiving ends of said "U" shaped lower band portion so that one or both ends of this "U" shaped lower band portion are inserted to a desired depth into said upper shoulder/setting portion so that the interior of the ring closes down on the finger sufficient to assure proper sensor contact on both the top and bottom surfaces of the finger;
- wherein one or both ends of said "U" shaped lower band portion is configured to electrically connect said circuit elements on said flexible circuit to said upper shoulder/setting portion; and
- wherein said plurality of bio-sensors are connected on a flexible circuit which extends from an area of said lower band on up to make electrical connection with circuitry within said upper shoulder/setting portion of the housing.

23. The apparatus as recited in claim 22, wherein a top surface of said upper shoulder/setting portion of the housing is configured for receiving one or more elements selected from the group of elements consisting of decorative elements, display indicators, and user input selectors.

24. The apparatus as recited in claim 22, wherein said power storage device is configured for being readily removed, so that another battery can be reinserted to increase time periods over which biometric data is collected by said biometric sensing ring apparatus.

25. The apparatus as recited in claim 22, wherein said plurality of sensors further comprise a chemical sensor configured for detecting certain chemical levels in user sweat.

* * * * *